US011351115B2

(12) United States Patent
Ledger et al.

(10) Patent No.: US 11,351,115 B2
(45) Date of Patent: Jun. 7, 2022

(54) INHALABLE PARTICLES

(71) Applicant: Crystec Ltd, Bradford (GB)

(72) Inventors: Daniel Mark Ledger, Bradford (GB); Linda Sharon Daintree, Leeds (GB); Peter York, West Runton (GB)

(73) Assignee: CRYSTEC LTD, Bradford (GB)

( * ) Notice: Subject to any disclaimer, the term of this patent is extended or adjusted under 35 U.S.C. 154(b) by 99 days.

(21) Appl. No.: 16/715,332

(22) Filed: Dec. 16, 2019

(65) Prior Publication Data

US 2020/0230053 A1 Jul. 23, 2020

Related U.S. Application Data

(63) Continuation of application No. 15/118,760, filed as application No. PCT/GB2015/050406 on Feb. 13, 2015, now abandoned.

(30) Foreign Application Priority Data

Feb. 13, 2014 (GB) ..................................... 1402556

(51) Int. Cl.
A61K 9/00 (2006.01)
A61K 31/137 (2006.01)

(52) U.S. Cl.
CPC .......... A61K 9/0075 (2013.01); A61K 31/137 (2013.01)

(58) Field of Classification Search
CPC .............................. A61K 9/0075; A61K 31/137
See application file for complete search history.

(56) References Cited

U.S. PATENT DOCUMENTS

| | | | | |
|---|---|---|---|---|
| 5,382,600 A ‡ | 1/1995 | Jonsson | .................. | C07C 43/23 514/60 |
| 5,559,269 A ‡ | 9/1996 | Johansson | ............... | A61P 25/02 564/44 |
| 7,005,449 B2 | 2/2006 | Hawley | | |
| 7,939,105 B2 ‡ | 5/2011 | Parikh | ..................... | A61P 37/06 424/49 |
| 8,206,746 B2 ‡ | 6/2012 | Parikh | ...................... | B82Y 5/00 252/36 |
| 8,273,330 B2 ‡ | 9/2012 | York | ..................... | A61K 9/1688 424/46 |
| 8,323,615 B2 ‡ | 12/2012 | Piran | .................. | B01D 11/0203 424/1 |
| 8,835,376 B2 ‡ | 9/2014 | Shen | ........................ | A61P 25/08 514/1 |
| 2003/0091513 A1 ‡ | 5/2003 | Mohsen | .................. | A61P 25/24 424/46 |
| 2003/0109421 A1 * | 6/2003 | Palakodaty | ................ | B01J 2/04 264/12 |
| 2003/0144352 A1 ‡ | 7/2003 | Cammarata | .......... | A61K 31/216 514/53 |
| 2003/0015703 A1 ‡ | 8/2003 | Chordia | ................. | A61K 9/145 424/46 |
| 2003/0232020 A1 | 12/2003 | York | | |
| 2005/0026848 A1 ‡ | 2/2005 | Robinson | ............... | A61K 31/56 514/26 |
| 2011/0132356 A1 ‡ | 6/2011 | Vehring | .................. | A61K 31/40 128/20 |
| 2011/0135737 A1 | 6/2011 | Vehring | | |
| 2011/0200678 A1 ‡ | 8/2011 | Hwang | .................... | A61P 31/04 424/48 |
| 2011/0308519 A1 ‡ | 12/2011 | Schiaretti | ............... | A61K 9/145 128/20 |
| 2012/0037232 A1 ‡ | 2/2012 | Shen | .................... | B01F 13/1027 137/1 |
| 2017/0056325 A1 | 3/2017 | Ledger | | |

FOREIGN PATENT DOCUMENTS

| | | | | |
|---|---|---|---|---|
| CN | 101756905 A ‡ | 6/2010 | | |
| EP | 1133284 B1 ‡ | 10/2004 | .......... | A61K 31/522 |
| EP | 1133285 B1 ‡ | 3/2006 | .............. | A61P 11/06 |
| EP | 1435909 B1 ‡ | 12/2009 | .............. | A61K 9/146 |
| EP | 1379337 B1 ‡ | 5/2012 | ................ | B01J 2/04 |
| EP | 1701932 B1 ‡ | 7/2012 | .............. | A61P 13/02 |
| EP | 2682099 A1 ‡ | 1/2014 | .............. | A61K 31/46 |
| EP | 2705838 A1 ‡ | 3/2014 | .............. | A61P 11/00 |
| KR | 20130078083 A ‡ | 7/2013 | | |
| WO | WO-1995/001221 A1 ‡ | 1/1995 | | |
| WO | WO-1996/000610 A1 ‡ | 1/1996 | | |
| WO | WO-1998/010649 A1 ‡ | 3/1998 | | |
| WO | WO-1998/029402 A1 ‡ | 7/1998 | | |
| WO | WO-1998/036825 A1 ‡ | 8/1998 | | |
| WO | WO-1999/044733 A1 ‡ | 9/1999 | | |
| WO | WO-1999/059710 A1 ‡ | 11/1999 | | |
| WO | WO-2001/003821 A1 ‡ | 1/2001 | | |
| WO | 2001014036 A1 | 3/2001 | | |
| WO | WO-2001/021154 A2 ‡ | 3/2001 | | |
| WO | WO-2001/045731 A1 ‡ | 6/2001 | | |
| WO | WO-2003/008082 A1 ‡ | 1/2003 | | |
| WO | WO-2003/035035 A1 ‡ | 5/2003 | | |
| WO | WO-2003/039464 A2 ‡ | 5/2003 | | |
| WO | WO-2003/090734 A1 ‡ | 11/2003 | | |
| WO | WO-2005/105043 A2 ‡ | 11/2005 | .............. | A61P 11/06 |
| WO | WO-2007/046001 A2 ‡ | 4/2007 | .......... | C07C 215/54 |
| WO | WO-2007/061529 A1 ‡ | 5/2007 | ................ | A61K 9/19 |
| WO | WO-2008/040094 A1 ‡ | 4/2008 | .............. | B01J 2/006 |
| WO | WO-2008/062429 A2 ‡ | 5/2008 | .............. | A61P 19/02 |
| WO | WO-2010/010464 A2 ‡ | 1/2010 | .............. | C07C 59/50 |
| WO | WO-2010/022282 A1 ‡ | 2/2010 | .............. | A61P 43/00 |
| WO | WO-2010/138862 A2 ‡ | 12/2010 | ......... | A61K 2300/00 |

(Continued)

OTHER PUBLICATIONS

Postlind, Hans, et al., "Tolterodine, A New Muscarinic Receptor Antagonist, Is Metabolized By Cytochromes P450 2D6 And 3A In Human Liver Microsomes." Drug Metabolism And Disposition, 1998, vol. 26, No. 4, pp. 289-293.‡

(Continued)

Primary Examiner — Mina Haghighatian

(74) Attorney, Agent, or Firm — Wenderoth, Lind & Ponack, L.L.P.

(57) ABSTRACT

A powder formulation, or pharmaceutical composition comprising or consisting of particles of an antimuscarinic agent, said particles being obtainable by supercritical anti-solvent (SAS) precipitation and having a $D_{50}$ of 4 μm or less and a $D_{90}$ of 10 μm or less. Methods of forming the formulation and composition are also disclosed, as are uses of the composition.

7 Claims, 14 Drawing Sheets

(56) References Cited

FOREIGN PATENT DOCUMENTS

| WO | WO-2012/098044 A1 ‡ | 7/2012 | ........... C07C 235/34 |
|---|---|---|---|
| WO | WO-2012/161492 A1 ‡ | 11/2012 | .......... A61K 31/4196 |
| WO | WO-2013/021199 A2 ‡ | 2/2013 | ........... A61K 31/205 |
| WO | WO-2014/118532 A1 ‡ | 8/2014 | ................ A61P 5/44 |
| WO | WO-2015/121664 A1 ‡ | 8/2015 | ........... A61K 9/0075 |

OTHER PUBLICATIONS

Ticehurst, Martyn D., et al., "Characterisation of the Influence of Micronisation on the Crystallinity and Physical Stability of Revatropate Hydrobromide." International Journal of Pharmaceutics, 2000, vol. 193, pp. 247-259.‡

Shekunov, B. Yu., et al., "Crystallization Process in Turbulent Supercritical Flows." Journal of Crystal Growth, 1999, vol. 198/199, pp. 1345-1351.‡

Okamoto, Hirokazu, et al., "Application of Supercritical Fluid to Preparation of Powders of High-Molecular Weight Drugs For Inhalation." Advanced Drug Delivery Reviews, 2008, vol. 60, pp. 433-446.‡

Kalani, Mahshid, et al., "Application of Supercritical Antisolvent Method In Drug Encapsulation: A Review." International Journal of Nanomedicine, 2011, vol. 6, pp. 1429-1442.‡

Reverchon, Ernesto, et al., "Mechanisms controlling supercritical antisolvent precipitate morphology." Chemical Engineering Journal, vol. 169, 2011, pp. 358-370.

\* cited by examiner
‡ imported from a related application

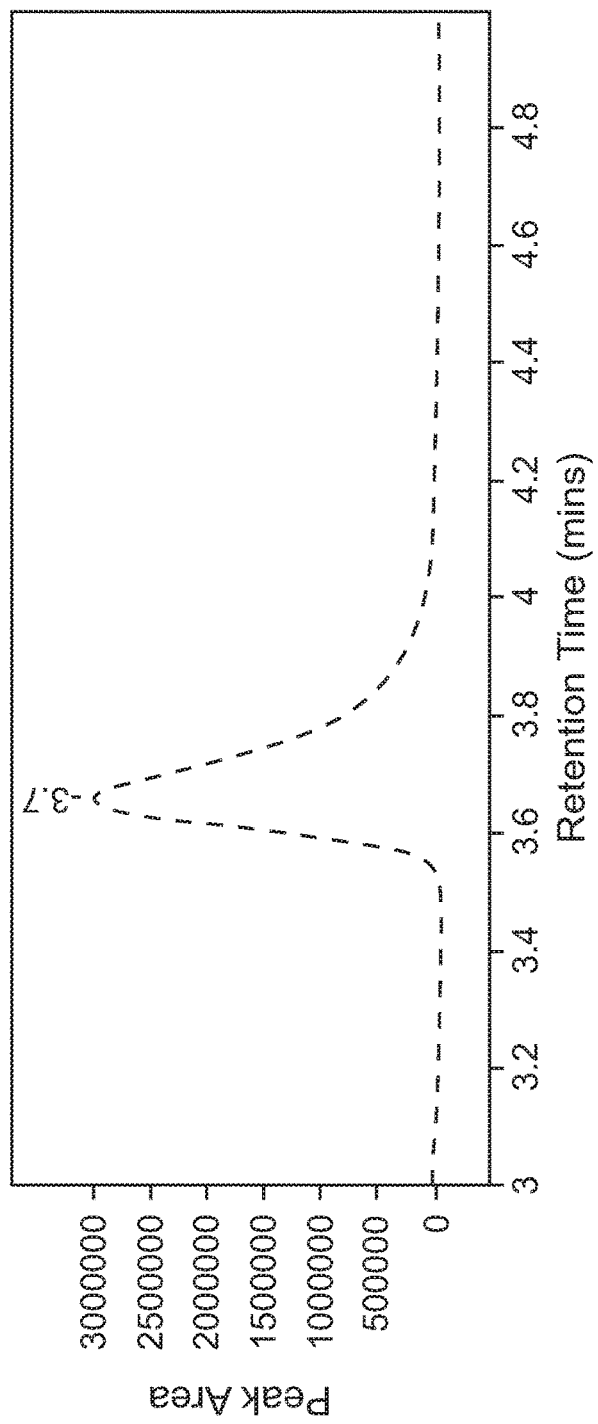
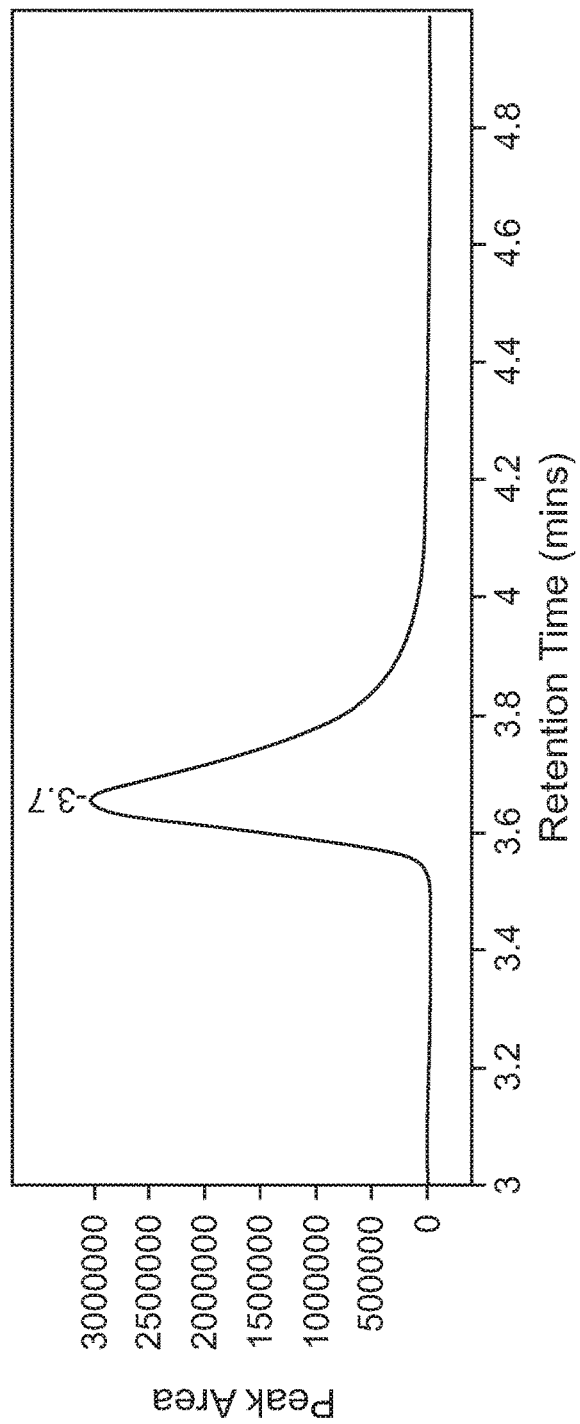

INHALABLE PARTICLES

FIELD OF THE INVENTION

This invention relates to powder formulations comprising an antimuscarinic agent, and to methods of forming such powder formulations.

In particular, though not exclusively, this invention relates to powder formulations comprising tolterodine, such as pharmaceutical powder compositions for administration by inhalation or insufflation, the use of such compositions as medicaments, as well as methods of treatment involving administration of the compositions. The compositions may be useful in particular for the treatment of urinary disorder, asthma, a group of breathing disorders termed Chronic Obstructive Pulmonary Disease (COPD), and allergic rhinitis.

BACKGROUND TO THE INVENTION

U.S. Pat. No. 5,382,600 discloses (substituted) 3,3-diphenylpropylamines useful for treating urinary incontinence. In particular, it discloses 2-[(1R)-3-(diisopropylamino)-1-phenylpropyl]-4-methylphenol, also known as N,N-diisopropyl-3-(2-hydroxy-5-methylphenyl)-3-phenylpropylamine, with the generic name of tolterodine, as being useful to treat urinary incontinence. Tolterodine is the compound of Example 22 of U.S. Pat. No. 5,382,600.

Tolterodine may be prepared, for example, as described in WO98/29402.

H Postlind et al, Drug Metabolism and Disposition, 26(4): 289-293 (1998) discloses that tolterodine is a muscarinic receptor antagonist. It is presently being sold in a number of different countries for treatment of urinary incontinence under the name Detrol®, as well as generically. When tolterodine is used to treat urinary incontinence it is administered perorally as a tablet. The major, active metabolite of tolterodine is the 5-hydroxymethyl derivative of tolterodine.

U.S. Pat. No. 5,559,269 and H Postlind et al, Drug Metabolism and Disposition, 26(4): 289-293 (1998) disclose hydroxytolterodine. U.S. Pat. No. 5,559,269 discloses this compound as being useful to treat urinary incontinence. Pharmacol. Toxicol., 81: 169-172 (1997) discloses that hydroxytolterodine has antimuscarinic activity.

WO98/29402 mentions tolterodine salts of the following acids: methanesulfonic, hydrochloric, hydrobromic, sulfuric, phosphoric, nitric, benzoic, citric, tartaric, fumaric, maleic, $CH_3—(CH_2)_n—COOH$ where n is 0 thru 4, and $HOOC—(CH_2)_n—COOH$ where n is as defined above.

The currently marketed administration form of tolterodine is film-coated tablets containing 1 mg, 2 mg or 4 mg of tolterodine L-tartrate for release in the gastrointestinal tract. Consumers constantly require alternative delivery forms with favourable efficacy and/or which simplify the treatment, thus improving their quality of life.

WO03/090734 discloses the use of tolterodine for treating asthma, COPD, and allergic rhinitis and suggests inhalable or insufflable compositions of tolterodine. This document discloses tolterodine salts of aliphatic mono- and dicarboxylic acids comprising from 7 to 24 carbon atoms, alkanedisulfonic acids comprising from 2 to 4 carbon atoms, and naphthoic acid derivatives comprising from 11 to 27 carbon atoms.

WO03/039464 discloses the use of inhalable or insufflable compositions of tolterodine for treating urinary disorder.

The preparation of inhalable or insufflable powder formulations comprising an antimuscarinic agent, in particular tolterodine, poses particular challenges. One issue faced in this area is that of unhelpful crystalline habits. For example, organic solvent particle precipitation/crystallisation of tolterodine L-tartrate leads to lengthy needle shaped (acicular) crystals, with the consequence that direct preparation of the particle sizes required for effective drug deposition in central and deep lung compartments is not possible by conventional crystallisation.

A conventional solution to preparing suitable powder formulations is to mill/micronise larger, acicular material. This approach, whilst producing particles in respirable ranges, generally results in highly charged, very cohesive material which causes severe downstream handling and processing issues. In addition, amorphous hygroscopic domains varying in content between batches of product tend to be formed which can lead to particle recrystallisation and growth upon uptake of water. As might be expected, being a random operation, milling produces irregular shaped and sized particle as a result of uncontrolled particle fracture and breakage.

A further problem with milling is that a disturbed particle size distribution is generally obtained. For example, a bimodal distribution may be obtained due to the presence of a proportion of primary particles, a significant amount of larger particles and a degree of agglomeration. It is also generally observed that for micronised powders a large number of smaller particles adhere to the surfaces of larger particles, due to the highly charged and energised surfaces after milling/micronisation. Such material will not aerosolise readily and easily.

It is an object of the invention to provide improved powder formulations comprising an antimuscarinic agent, in particular tolterodine, and/or to solve at least one problem associated with the prior art, e.g. as set out hereinabove.

STATEMENTS OF THE INVENTION

Aspects and embodiments of the invention embrace powder formulations comprising or consisting of particles of an antimuscarinic agent.

Advantageously, the particles of antimuscarinic agent may have a $D_{50}$ of 4 µm or less and a $D_{90}$ of 10 µm or less. Such particles have been found to be readily inhalable or insufflable, and can be obtained by supercritical anti-solvent (SAS) precipitation to particularly facilitate inhalation or insufflation.

It has been found that SAS precipitation of antimuscarinic agents can provide particles that are more readily inhalable than milled particles.

Without wishing to be bound by theory, it appears that SAS precipitation leads to antimuscarinic particles with more readily inhalable shapes and sizes. The highly charged and energised surfaces seen in milled particles can be avoided.

This can offer significant clinical advantages, e.g. by reducing required dose and/or facilitating rapid onset.

According to a first aspect of the invention, there is provided a powder formulation comprising or consisting of particles of an antimuscarinic agent, said particles being obtainable or obtained by supercritical anti-solvent (SAS) precipitation and having a $D_{50}$ of 4 μm or less and a $D_{90}$ of 10 μm or less.

As is known in the art, $D_{50}$ is the particle diameter where a cumulative particle diameter distribution reaches 50% by volume, i.e. 50% by volume of the particles have a smaller diameter than this value, and 50% by volume of the particles have a larger diameter than this value. Similarly, $D_{90}$ is the particle diameter where a cumulative diameter distribution reaches 90% by volume, i.e. 90% by volume of the particles have a smaller diameter than this value, and 10% by volume of the particles have a larger diameter than this value.

All particle sizes (diameters) herein are volume based particle diameters, measured for example by laser diffraction, and relate to the maximum particle diameter. Particle diameters may be determined using a Sympatec Helos™ laser diffraction particle size analyser fitted with a Aspiros™ dry powder microdosing system, using an aerosolisation pressure of 4 bar.

Suitably, the powder formulation may be a dry powder formulation. The powder formulation may be suitable for inhalation and/or insufflation. The powder formulation may advantageously comprise, or consist of, antimuscarinic agent particles having a $D_{50}$ of 4 μm or less, or 3.5 μm or less, or 3 μm or less, or 2.5 μm or less, or 2 μm or less; and/or having a $D_{90}$ of 10 μm or less, or 8 μm or less, or 6 μm or less, or 5 μm or less.

In principle, the $D_{50}$ and $D_{90}$ may be as low as possible. However, a narrow distribution of particle diameters aids aerosolisation. In an embodiment, the $D_{50}$ is 1 μm or more. In an embodiment, the $D_{90}$ is 2 μm or more.

Suitably, the volume mean diameter of the particles of antimuscarinic agent may be 7 μm or less, in particular 5 μm or less, or even 3 μm or less.

Advantageously, the particles of antimuscarinic agent may have a monomodal particle size distribution.

Antimuscarinic agents are muscarinic receptor antagonists, i.e. agents that block the activity of the muscarinic acetylcholine receptor. Antimuscarinic agents may be non-selective or selective to one or more muscarinic receptor subtypes, of which five ($M_1$ to $M_5$) have been determined. In an embodiment, the antimuscarinic agent acts on the $M_2$ and $M_3$ subtypes.

In an embodiment, the antimuscarinic agent is tolterodine or a tolterodine-related compound, or a pharmaceutically acceptable salt thereof.

As mentioned above, the chemical name of tolterodine is (R)—N, N-diisopropyl-3-(2-hydroxy-5-methylphenyl)-3-phenylpropanamine. The term "tolterodine-related compound" is meant to encompass the major, active metabolite of tolterodine, i.e. (R)—N, N-diisopropyl-3-(2-hydroxy-5-hydroxymethylphenyl)-3-phenylpropanamine ("hydroxytolterodine"); the corresponding (S)-enantiomer to tolterodine, i.e. (S)—N, N-diisopropyl-3-(2-hydroxy-5-methylphenyl)-3-phenylpropanamine; the 5-hydroxymethyl metabolite of the (S)-enantiomer, i.e. (S)—N, N-diisopropyl-3-(2-hydroxy-5-hydroxymethylphenyl)-3-phenylpropanamine; as well as the corresponding racemate to tolterodine, i.e. (R, S)—N, N-diisopropyl-3-(2-hydroxy-5-methylphenyl)-3-phenylpropanamine; and prodrug forms thereof. An example of a prodrug form is fesoterodine (2-[(1R)-3-(Di(propan-2-yl)amino)-1-phenylpropyl]-4-(hydroxymethyl)phenyl] 2-methylpropanoate), which is bioactivated to hydroxytolterodine.

In an embodiment, the antimuscarinic agent comprises tolterodine.

In an embodiment, the antimuscarinic agent is a salt of tolterodine or a tolterodine-related compound and one of the following acids: methanesulfonic, hydrochloric, hydrobromic, sulfuric, phosphoric, nitric, benzoic, citric, tartaric, fumaric, maleic, $CH_3—(CH_2)_n—COOH$ where n is 0 to 4, and $HOOC—(CH_2)_n—COOH$ where n is 0 to 4, aliphatic mono- and dicarboxylic acids comprising from 7 to 24 carbon atoms, alkanedisulfonic acids comprising from 2 to 4 carbon atoms, and naphthoic acid derivatives comprising from 11 to 27 carbon atoms. In an embodiment the antimuscarinic agent is a tartrate, in particular an L-tartrate salt.

The particles of antimuscarinic agent may consist essentially or entirely of antimuscarinic agent.

In an embodiment the particles of antimuscarinic agent are in crystalline form. By crystalline form is meant any form of the antimuscarinic agent that is essentially free and preferably entirely free of amorphous portions of the antimuscarinic agent. By "essentially free of amorphous portions" is meant that the form contains less than 10% by weight, preferably less than 5% by weight, and most preferably less than 1% by weight antimuscarinic agent in an amorphous form, wherein the weight percentages relate to the total amount of antimuscarinic agent. Crystalline portions of an antimuscarinic agent may be characterized for example by DSC measurement and/or Powder X-ray Diffraction (PXRD) as is known in the art. Taking the example of tolterodine L-tartrate, crystalline particles of this salt are readily distinguishable by having a sharp melting endotherm of 214 to 216° C. (onset) that decomposes on melt.

Particular advantages arise from SAS precipitation in the context of crystal habits that are not conducive to the formation of inhalable particles. In an embodiment, the antimuscarinic agent has an acicular crystal habit under solvent evaporation crystallization conditions. By an acicular crystal habit is meant that the antimuscarinic agent forms, under conventional solvent evaporation crystallisation conditions, crystals with a length in one dimension that is at least 4 times, such as at least 6 times, or even at least 8 times, the length in any other dimension. Typically the crystals are needle-shaped.

It has been found that SAS precipitation can advantageously overcome the problems associated with acicular crystal habits and milling, enabling more effective delivery of antimuscarinic agents with an acicular crystal habit.

In an embodiment, the antimuscarinic agent is tolterodine L-tartrate. As aforesaid, organic solvent particle precipitation/crystallisation of tolterodine L-tartrate leads to the formation of acicular crystals unsuitable for inhalation or insufflation. This compound has an acicular crystal habit under solvent evaporation crystallization conditions. However, it has now been found that particles exhibiting a reduced length needle-shaped habit ("torpedo shaped" beneficial for facile fluidisation and aerosolisation) and having an inhalable or insufflable particle size can be obtained by SAS precipitation of tolterodine L-tartrate.

Advantageous powder formulations comprising or consisting of particles of an antimuscarinic agent may be formed by SAS precipitation of said particles. Limitations and problems associated with milling/micronising, for example as described hereinabove, may be avoided. As is known in the art, SAS precipitation involves contacting a supercritical or near critical anti-solvent (fluid) with a solution, in the present case a solution of an antimuscarinic agent. Contacting of the anti-solvent with the solution leads to supersaturation and particle precipitation.

Aspects and embodiments of the invention embrace anti-solvent precipitation methods, in particular SAS precipitation methods, of forming powder formulations comprising or consisting of particles of an antimuscarinic agent.

The powder formulation according to the first aspect may suitably be obtainable, or obtained by any anti-solvent precipitation method of any aspect or embodiment of the invention.

According to a second aspect of the invention, there is provided a method of forming a powder formulation, the method comprising contacting a fluid anti-solvent with a solution of antimuscarinic agent to precipitate particles of antimuscarinic agent. The powder formulation, antimuscarinic agent and/or particles may be as defined or described hereinabove in relation to foregoing aspects of the invention.

The anti-solvent may in principle be any fluid consistent with achieving desired particle formation. As is known in the art, an anti-solvent for precipitation is generally chosen such that the product, in this case the antimuscarinic agent, is substantially insoluble therein. The role of the anti-solvent is thus to extract the solvent from the solution of antimuscarinic agent and to precipitate particles of antimuscarinic agent. An example of a suitable anti-solvent is carbon dioxide.

In an embodiment, the anti-solvent is a supercritical fluid, although in some embodiments near-critical fluids may also be suitable. A "supercritical fluid" is a fluid at or above its critical pressure (Pc) and critical temperature (Tc) simultaneously. In practice, the pressure of the fluid is likely to be in the range between 1.01 and 7.0 of its critical pressure, and its temperature in the range between 1.01 and 4.0 of its critical temperature (in Kelvin). However, some fluids (e.g., helium and neon) have particularly low critical pressures and temperatures, and may need to be used under operating conditions well in excess of those critical values, such as up to 200 times the relevant critical value. The term "near-critical fluid" encompasses both high pressure liquids, which are fluids at or above their critical pressure but below (although preferably close to) their critical temperature, and dense vapors, which are fluids at or above their critical temperature but below (although preferably dose to) their critical pressure. By way of example, a high pressure liquid might have a pressure between about 1.01 and 7 times its Pc, and a temperature between about 0.5 and 0.99 times its Tc. A dense vapour might, correspondingly, have a pressure between about 0.5 and 0.99 times its Pc, and a temperature between about 1.01 and 4 times its Tc.

In an embodiment, the fluid anti-solvent and the solution of antimuscarinic agent may form a supercritical or near-critical mixture on contact.

In an embodiment, the anti-solvent is carbon dioxide having a pressure in the range of from 75 to 150 bar absolute. In an embodiment, the carbon dioxide has a temperature in the range of from 35 to 80° C.

In an embodiment, the anti-solvent has a density in the range of from 0.20 to 0.75 g/cm$^3$. In an embodiment, the anti-solvent has a density in the range of from 0.30 to 0.75 g/cm$^3$, e.g. in the range of from 0.30 to 0.50 g/cm$^3$, in particular in the range of from 0.30 to 0.40 g/cm$^3$.

In an embodiment, a high excess of the anti-solvent is contacted with the solution of antimuscarinic agent. For example, the ratio of the mass fraction of contacted anti-solvent to the mass fraction of contacted tolterodine solution may be 30 or more, or advantageously 200 or more.

In an embodiment the ratio of the mass fraction of contacted anti-solvent to the mass fraction of contacted tolterodine solution is 30 or more and the fluid anti-solvent has a density in the range of from 0.30 to 0.75 g/cm$^3$.

Formulations comprising or consisting of advantageously inhalable or insufflable particles of an antimuscarinic agent can be formed under particular precipitation conditions.

According to a third aspect of the invention, there is provided a method of forming a powder formulation comprising or consisting of an antimuscarinic agent, in particular tolterodine L-tartrate, the method comprising: contacting a stream of anti-solvent with a stream of tolterodine L-tartrate solution to form particles of antimuscarinic agent, the stream of anti-solvent having a density in the range of from 0.20 to 0.75 g/cm$^3$, wherein: (i) the ratio of the mass fraction of contacted anti-solvent to the mass fraction of contacted tolterodine solution is 30 or more and the anti-solvent has a density in the range of from 0.30 to 0.75 g/cm$^3$; and/or (ii) the ratio of the mass fraction of contacted anti-solvent to the mass fraction of contacted tolterodine solution is 200 or more. The anti-solvent may suitably be carbon dioxide, in particular supercritical or near-critical carbon dioxide, as aforesaid.

Advantageously, it has been found that, when the ratio of the mass fraction of contacted anti-solvent to the mass fraction of contacted tolterodine solution is 30 or more and the anti-solvent has a density in the range of from 0.30 to 0.75 g/cm$^3$; and/or (ii) the ratio of the mass fraction of contacted anti-solvent to the mass fraction of contacted tolterodine solution is 200 or more, it is possible to produce particles of tolterodine L-tartrate that have a $D_{50}$ of 4 μm or less and a $D_{90}$ of 10 μm or less. Such particles have been found to be readily inhalable or insufflable.

In methods of the invention, the solution of antimuscarinic agent may be prepared in any suitable manner and in any suitable solvent system. In an embodiment, the solution comprises 5 mg/ml or more of antimuscarinic agent, suitably 10 mg/ml or more of antimuscarinic agent (based on the volume of solvent system in the solution at standard atmosphere and pressure). The maximum amount of antimuscarinic agent in the solution is generally limited only by the solubility of the agent in the solvent system. In an embodiment, the solution comprises 100 mg/ml or less, suitably 50 mg/ml or less of antimuscarinic agent (based on the volume of solvent system in the solution at standard atmosphere and pressure).

The solvent system of the solution may be chosen consistent with the solubility of the antimuscarinic agent. In an embodiment the solvent system comprises an organic solvent. Suitably, the solvent system may comprise an alcohol. For example, the solvent system may comprise or consist of methanol, especially where the antimuscarinic agent comprises tolterodine, in particular tolterodine L-tartrate.

The anti-solvent and the solution of antimuscarinic agent may be contacted in any manner consistent with desired particle formation. In general, to achieve precipitation, the anti-solvent and solution are contacted such that extraction of a solvent system of the solution occurs by the action of the anti-solvent. Suitably, this may occur in a precipitation chamber, for example a chamber in which temperature and pressure may be controlled to desired levels. Mixing energy may be provided by shear between the anti-solvent and the solution, as is known in the art. Advantageously, the anti-solvent and solution may be contacted such that dispersion and extraction of the solvent system occur substantially simultaneously by the action of the anti-solvent. Suitably, the energy of mixing may be arranged to provide a virtually instantaneous homogeneous fluid mixture of the anti-solvent and solution.

In an embodiment, the method comprises contacting a relatively high velocity anti-solvent stream, with a relatively low velocity stream solution of antimuscarinic agent. The relative velocities of the two fluid streams may suitably be managed by varying the diameter and cross sectional area of respective jets or nozzles for delivering the streams, and controlling the flow rate of each fluid stream. For example, the velocity of a stream may be controlled by an orifice plate of fixed diameter. This diameter may be arranged so as to maintain a set temperature and pressure on the upstream side of the orifice plate, while maintaining a specific flow rate through the orifice. The velocity of the resulting stream can be calculated using the density of the fluid upstream of the orifice plate (by referencing the fluid temperature and pressure), the mass flow of the fluid, the cross sectional area of the orifice, and the differential pressure across the orifice (equation given in Crystallization process in turbulent supercritical flows, Shekunov, B Yu, Hanna M, York P J Crystal Growth, 198-199, 1345-1351 (1999)).

The amount of kinetic energy suitable for mixing the two fluid streams and initiating supersaturation varies between each solute and each solvent mixture used. In an embodiment, the anti-solvent velocity is in the range of from 12 to 360 m/sec$^{-1}$. The velocity of the solution of antimuscarinic agent is typically lower than the velocity of the anti-solvent stream and not critical to the invention. In an embodiment, the velocity ratio between the anti-solvent stream and the solution is in the range of from 500:1 to 1000:1.

Suitably, the anti-solvent and solution may be introduced into a precipitation chamber via respective passages with respective outlets, the outlets being arranged relative to one another such that anti-solvent introduced through a first passage and solution introduced through a second passage both enter the precipitation chamber at substantially the same point, which is substantially the point at which the anti-solvent and solution meet. To provide for good levels of mixing and dispersion, the anti-solvent and the solution may, for example, be co-fed into a precipitation chamber via a nozzle having co-axial passages which terminate adjacent to one another. Alternatively, one or more streams of the anti-solvent may be arranged to impinge on a stream of the solution to provide good levels of mixing and dispersion. However, other mixing architectures are also possible. Examples of suitable apparatus are known, inter alia, from WO-95/01221, WO-96/00610, WO-98/36825, WO-99/44733, WO-99/59710, WO-01/03821, and WO-03/008082, which are incorporated herein by reference.

Aspects of the invention embrace pharmaceutical compositions comprising or consisting of a therapeutically effective amount of a powder formulation according to the invention, e.g. as described hereinabove, or as obtainable by a method according to the invention, e.g. as described hereinabove.

From a fourth aspect, the invention provides a pharmaceutical composition comprising or consisting of a therapeutically effective amount of particles of an antimuscarinic agent, said particles being obtainable by supercritical anti-solvent (SAS) precipitation and having a $D_{50}$ of 4 μm or less and a $D_{90}$ of 10 μm or less.

In an embodiment, the pharmaceutical composition is a dry powder composition. However, the composition may take any suitable forms known in the art. Suitably, the particles may be suspended in a non-solvent vehicle.

In an embodiment, the pharmaceutical composition has the form of a physical mixture and comprises a suitable pharmaceutical excipient for the particles of antimuscarinic agent.

In an embodiment, the pharmaceutical composition comprises an excipient. Suitable amounts of excipient are known to a skilled person. For example, one or more excipients may be present in an amount of from 50 to 99% by weight of the total composition, suitably 60 to 95% by weight of the total composition. The excipient may be of conventional type and may be obtained by any suitable process. An example of a suitable excipient is inhalable lactose.

Suitably, the pharmaceutical composition may comprise a formulation and/or particles as described or defined in respect of foregoing aspects of the invention. In an embodiment, the pharmaceutical composition comprises or consists of particles of tolterodine L-tartrate.

From a fifth aspect of the invention, there is provided the use of a pharmaceutical composition according to the invention, e.g. as described hereinabove, as a medicament. In some embodiments, the pharmaceutical compositions may be for treating, in a human or other mammal, a disorder selected from the group consisting of: urinary disorder, asthma, COPD, and allergic rhinitis. In a preferred embodiment, the treatment is by inhalation or insufflation. In an embodiment, the treatment is by pulmonary delivery.

In an embodiment, the disorder may be one requiring rapid relief, e.g. rapid symptomatic relief, or fast onset of the antimuscarinic agent. The treatment may thus be for providing rapid relief, e.g. rapid symptomatic relief, or onset of the antimuscarinic agent within a short period of time, e.g. less than 10 minutes, or less than 5 minutes, or less than 2 minutes, or less than 30 seconds. Rapid relief or fast onset may, for example, be defined as achieving at least 50% of peak plasma exposure to the antimuscarinic agent, more preferably at least 70% of peak plasma exposure to the antimuscarinic agent within the relevant time. Additionally or alternatively, rapid relief or fast onset may be defined as an improvement of at least 10%, preferably at least 20%, more preferably at least 30% or even at least 40% in at least one grading system associated with the disorder within the relevant time. Examples of a suitable grading system for urinary disorders are the urgency perception score "UPS" (J Urol. 2007 January; 177(1):199-202), the Indevus Urgency Severity Scale "IUSS" (J Urol. 2005 August; 174(2):604-7), or the patient perception of intensity of urgency scale "PPIUS" (BMC Urology 2012, 12:26). Other suitable grading systems are also known in the art.

In an embodiment, the pharmaceutical composition may be for treating urinary incontinence, in particular urge incontinence, stress incontinence or mixed incontinence. Treatment of such symptoms/disorders benefits particularly from rapid relief.

From a sixth aspect of the invention, there is provided a method of treating a disorder in a human or other mammal, comprising administering to said human or other mammal in need of such a treatment, a therapeutically effective amount of a pharmaceutical composition according to the invention. In a preferred embodiment, said administration is performed by inhalation or insufflation.

The pharmaceutical compositions of the invention may in particular be optimized for the treatment of urinary disorder, in particular urge incontinence, stress incontinence or mixed incontinence, by inhalation or insufflation.

From a seventh aspect, there is provided a dry pharmaceutical powder composition comprising or consisting of particles of tolterodine L-tartrate, said particles being obtainable by supercritical anti-solvent (SAS) precipitation and having a $D_{50}$ of 4 μm or less and a $D_{90}$ of 10 μm or less, for the treatment of urinary disorder by inhalation or insufflation.

Aspects of the invention embrace particular amounts of the powder formulations and pharmaceutical powder compositions. From an eighth aspect, the invention resides in an amount of at least 0.1 mg, in particular at least 0.2 mg, or even at least 1 mg of a powder formulation or pharmaceutical composition according to the invention or as obtainable by a method according to the invention.

Aspects of the invention embrace inhalation or insufflation devices comprising a pharmaceutical composition according to the invention.

From a ninth aspect, the invention resides in an inhalation or insufflation device, for example a metered-dose inhaler or a dry powder inhaler, having therein for dispense a pharmaceutical composition according to the invention or as obtainable by a method according to the invention.

Throughout the description and claims of this specification, the words "comprise" and "contain" and variations of the words, for example "comprising" and "comprises", mean "including but not limited to", and do not exclude other moieties, additives, components, integers or steps. Moreover the singular encompasses the plural unless the context otherwise requires: in particular, where the indefinite article is used, the specification is to be understood as contemplating plurality as well as singularity, unless the context requires otherwise.

Features of each aspect of the invention may be as described in connection with any of the other aspects. Other features of the invention will become apparent from the following examples. Generally speaking the invention extends to any novel one, or any novel combination, of the features disclosed in this specification (including any accompanying claims and drawings). Thus features, integers, characteristics, compounds, chemical moieties or groups described in conjunction with a particular aspect, embodiment or example of the invention are to be understood to be applicable to any other aspect, embodiment or example described herein unless incompatible therewith. Moreover unless stated otherwise, any feature disclosed herein may be replaced by an alternative feature serving the same or a similar purpose.

Where upper and lower limits are quoted for a property, then a range of values defined by a combination of any of the upper limits with any of the lower limits may also be implied.

In this specification, references to properties are—unless stated otherwise—to properties measured under standard temperature and pressure, i.e. at atmospheric pressure and at a temperature of 20° C.

The present invention will now be further described with reference to the following non-limiting examples and the accompanying illustrative drawings, of which:

FIGS. 4a and 4b are respectively HPLC traces for tolterodine L-tartrate (starting material) and tolterodine L-tartrate particles precipitated in Example 1;

Figure 8:
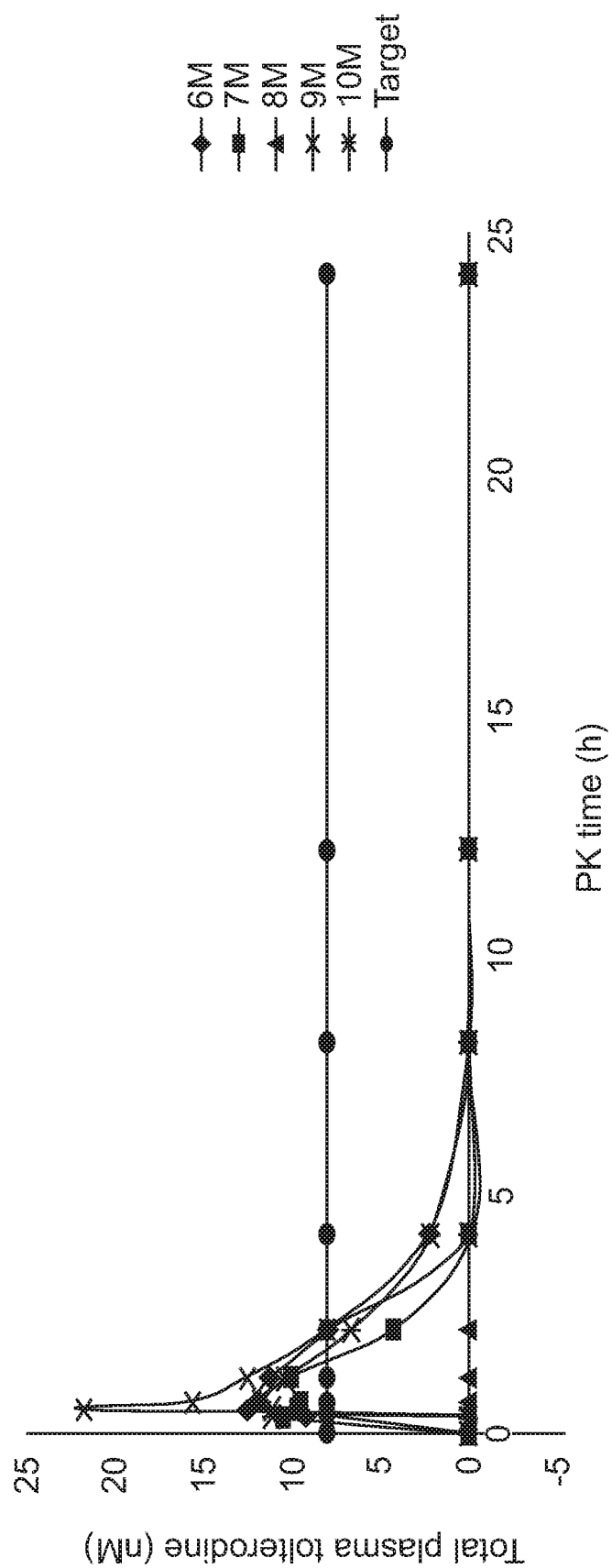
Figure 9:
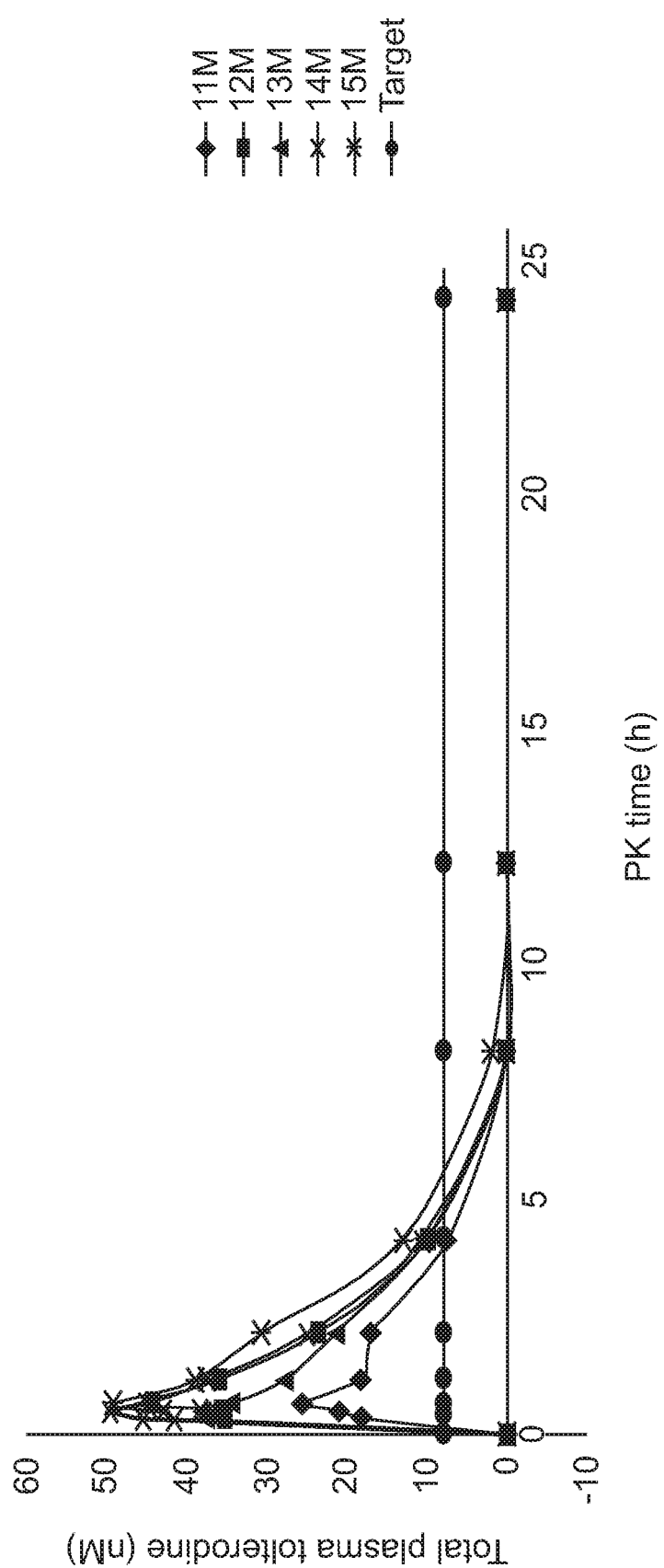
Figure 10A:
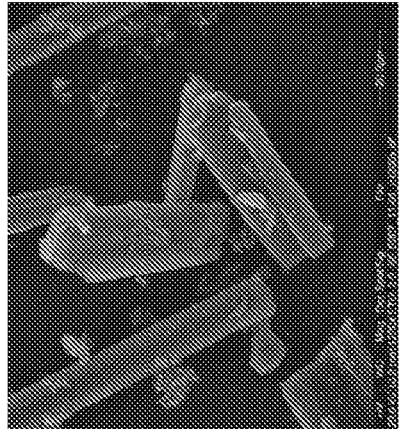
Figure 10B:
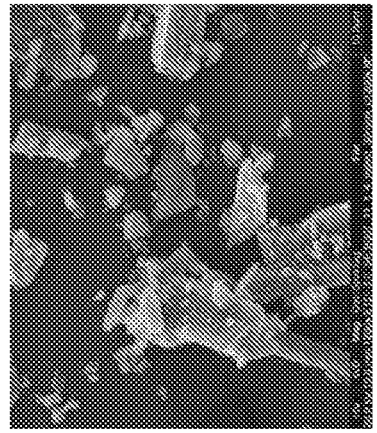
Figure 10C:
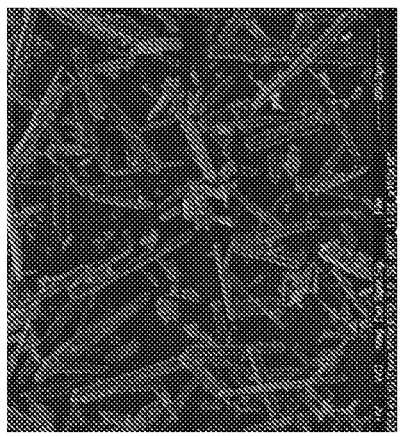
Figure 10D:
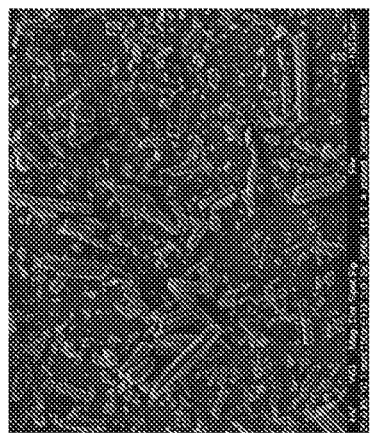

FIG. 8 pharmacokinetic data for Group 2 (0.3 mg/kg dose for 10 minutes) in Example 32;

FIG. 9 shows pharmacokinetic data for Group 3 (1.0 mg/kg dose for 10 minutes) in Example 32;

FIGS. 10a and 10b are SEMs of tolterodine L-tartrate particles formed by conventional solvent evaporation crystallisation; and FIGS. 10c and 10d are SEMs of the tolterodine L-tartrate particles of FIGS. 10a and 10b respectively following milling.

EXAMPLES

Comparative Example (Milling)

With reference to FIGS. 10a to 10d, a conventional solution to preparing powder formulations is to mill/micronise larger, acicular material. This approach, whilst producing particles in respirable ranges, generally results in highly charged, very cohesive materials which causes severe downstream handling and processing issues.

Referring now to FIGS. 10c and 10d, as might be expected, being a random operation, milling produces irregular shaped and sized particle as a result of uncontrolled particle fracture and breakage.

Figure 1:
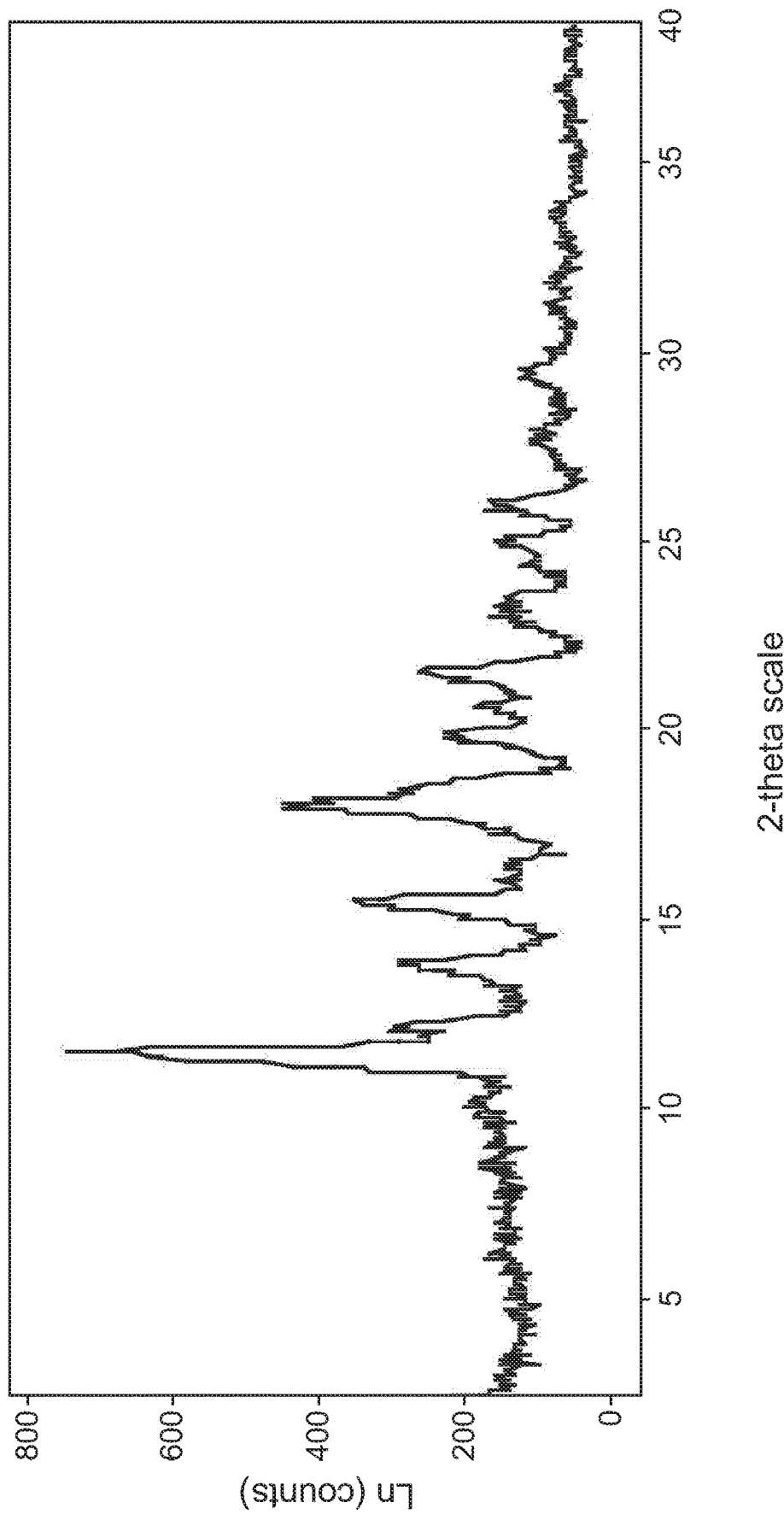
FIG. 1 is a PXRD analysis of tolterodine L-tartrate particles precipitated in Example 1.
Figure 2A:
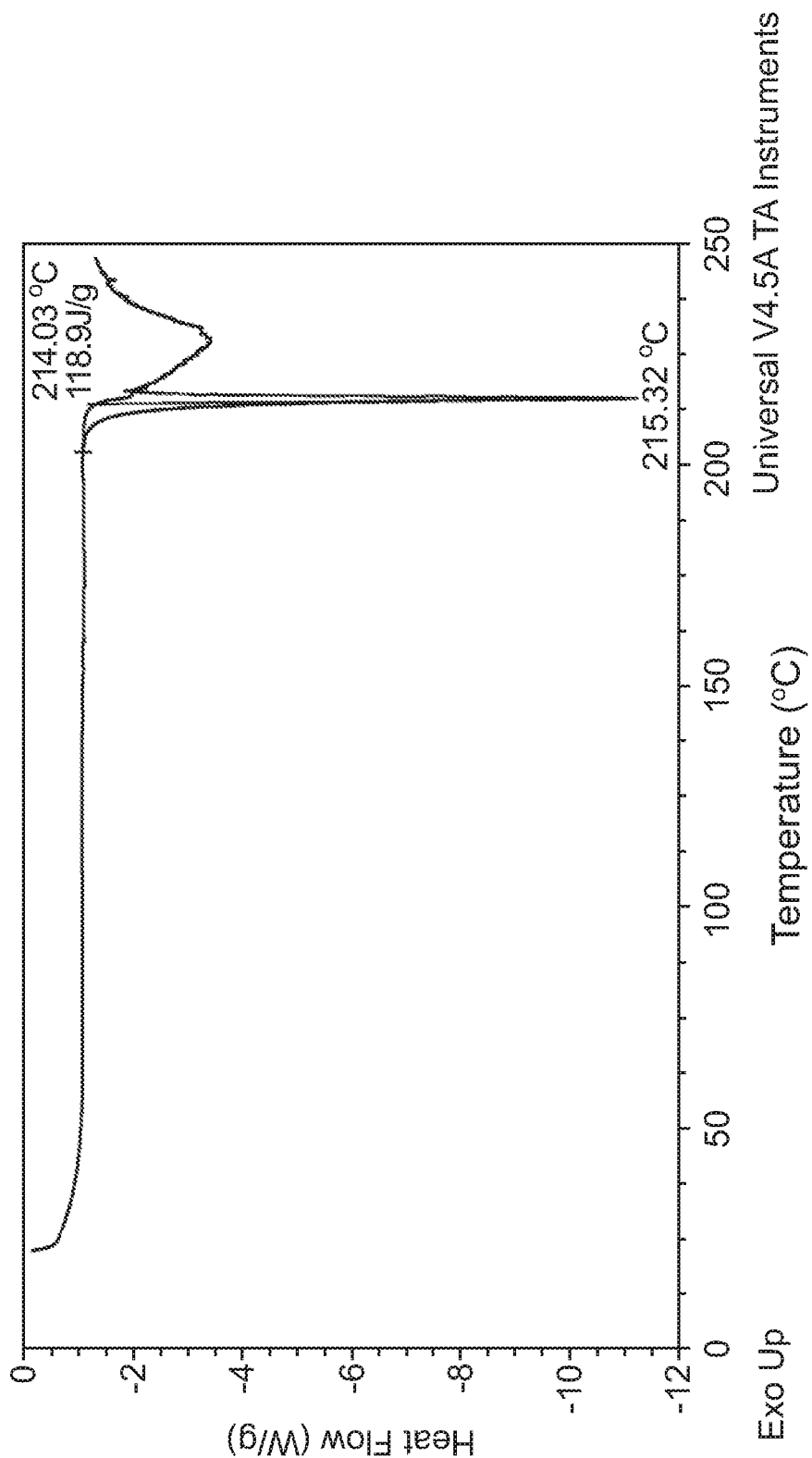
FIGS. 2a and 2b show a thermal analysis of tolterodine L-tartrate particles precipitated in Example 1.
Figure 2B:
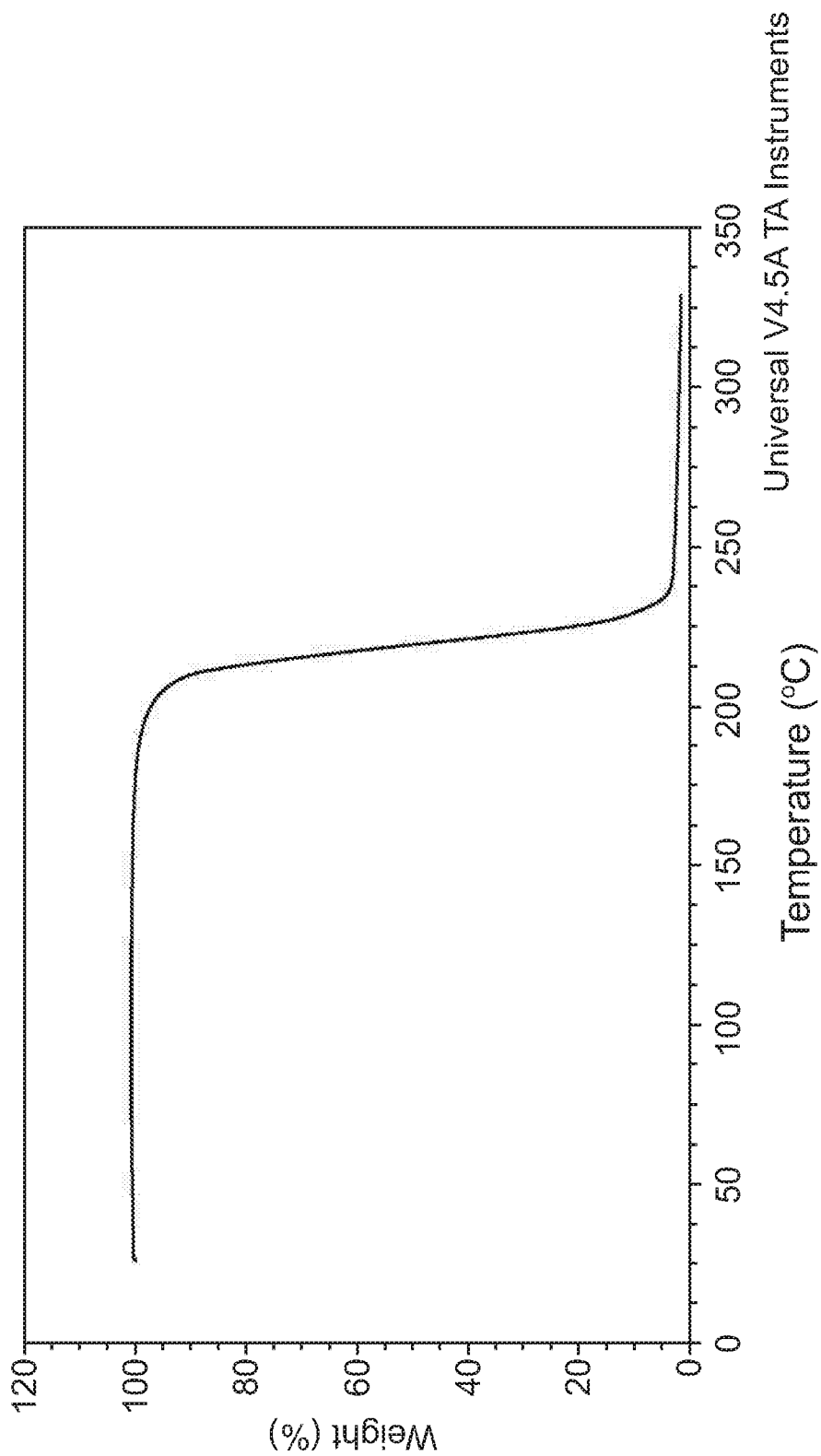
Figure 3A:
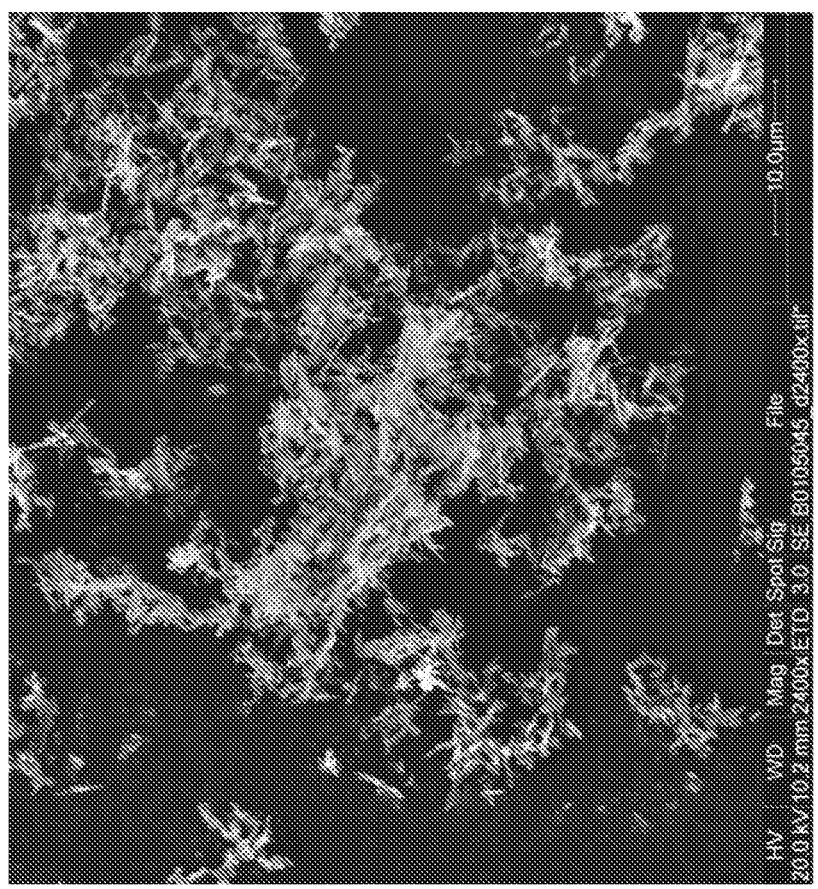
FIG. 3a is an SEM of tolterodine L-tartrate particles precipitated in Example 1.
Figure 3B:
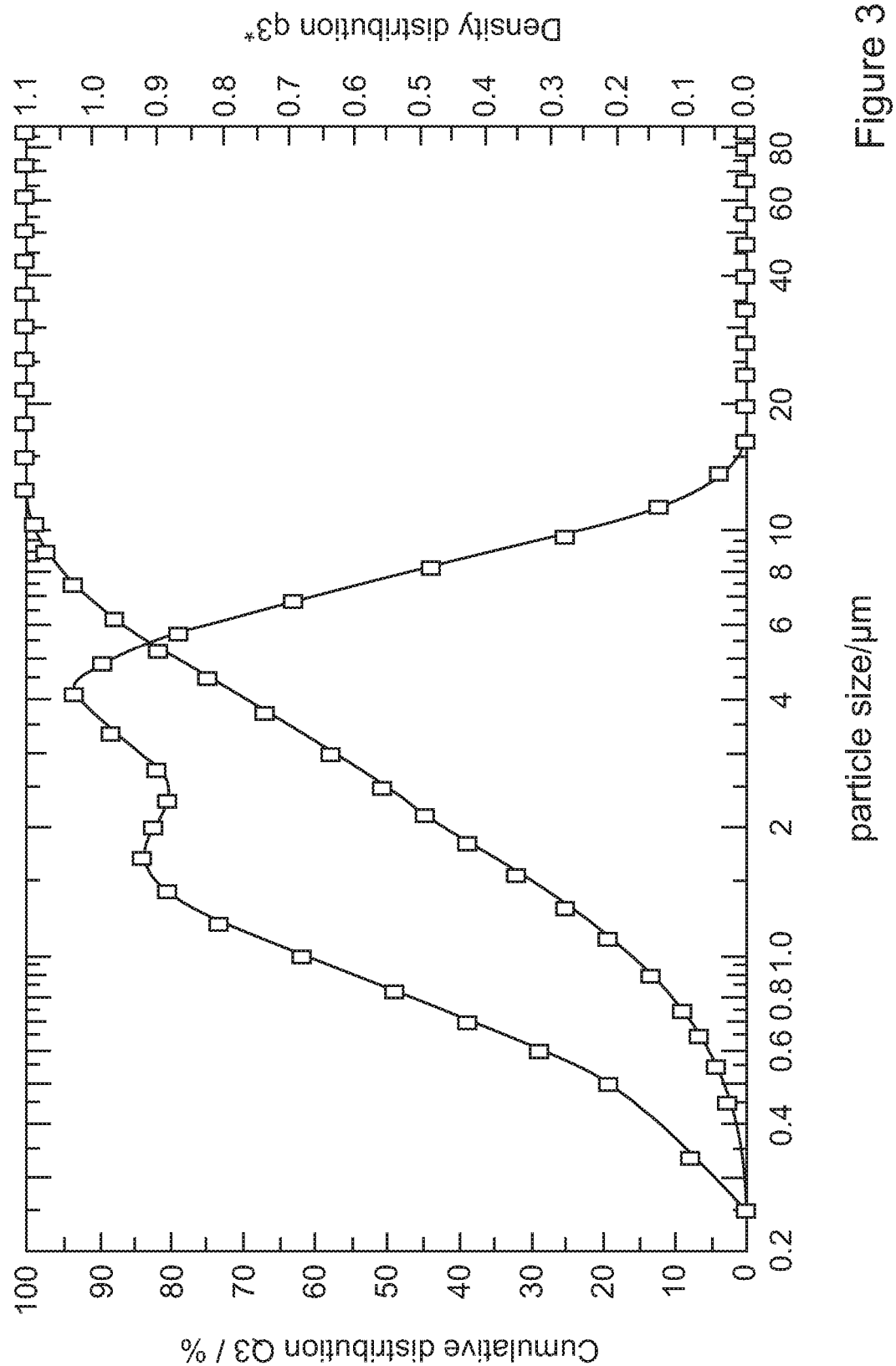
FIGS. 3b and 3c are respectively particle size analyses of milled tolterodine L-tartrate, and tolterodine L-tartrate particles precipitated in Example 1.
Figure 3C:
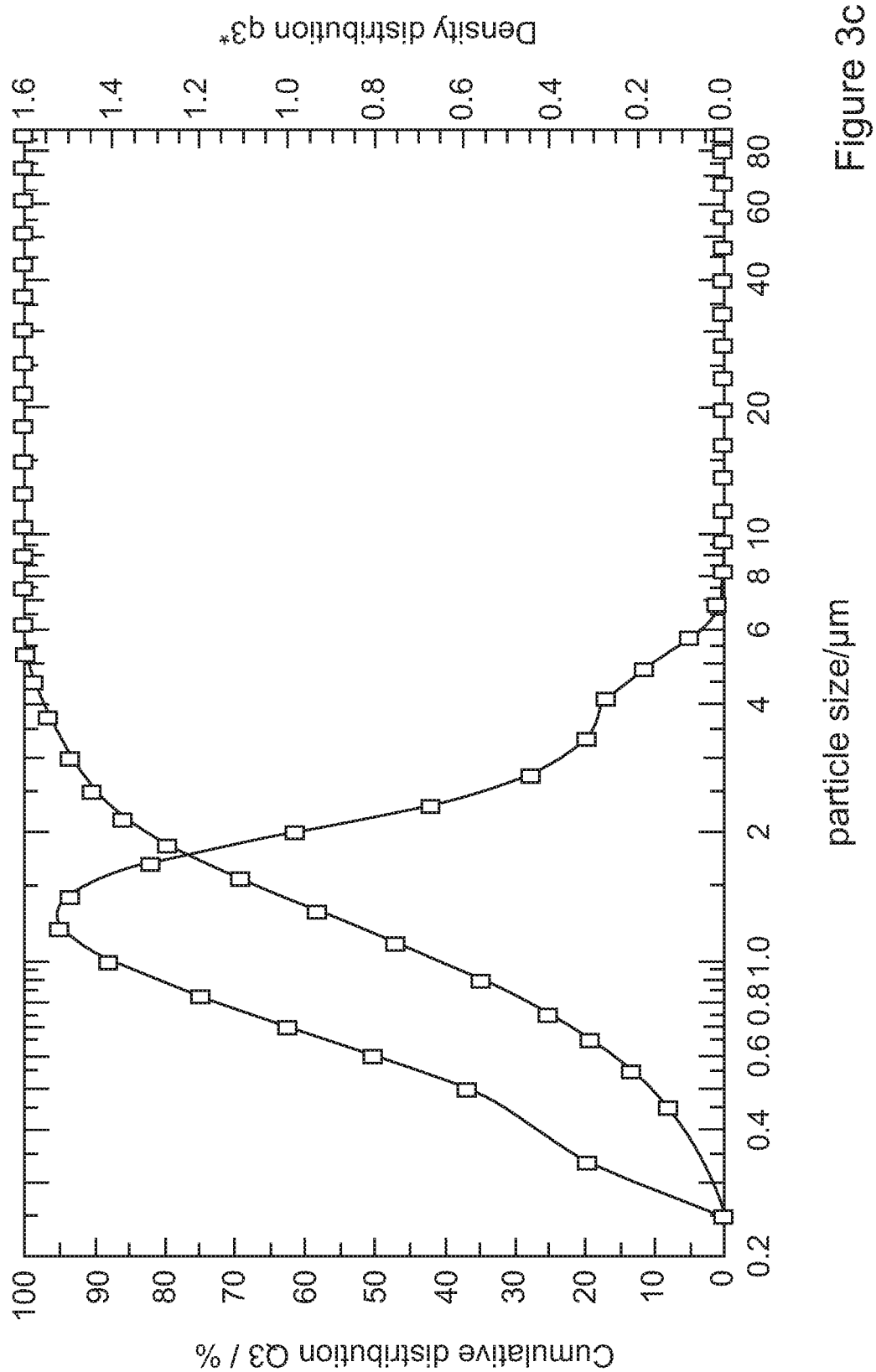
Figure 5B:
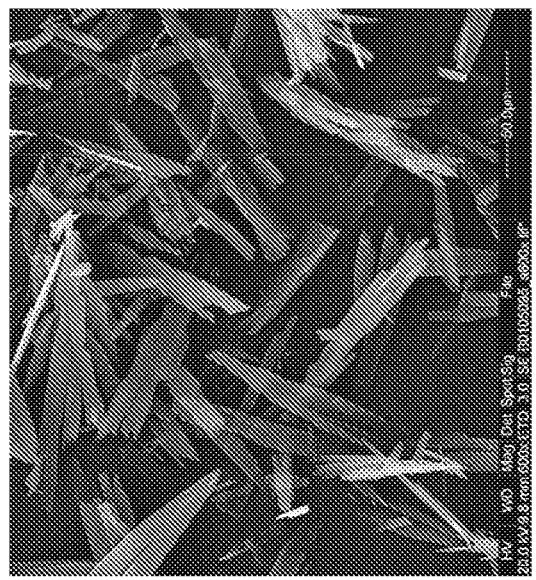
FIG. 5b is an SEM of tolterodine L-tartrate particles precipitated in Example C2.
Figure 5A:
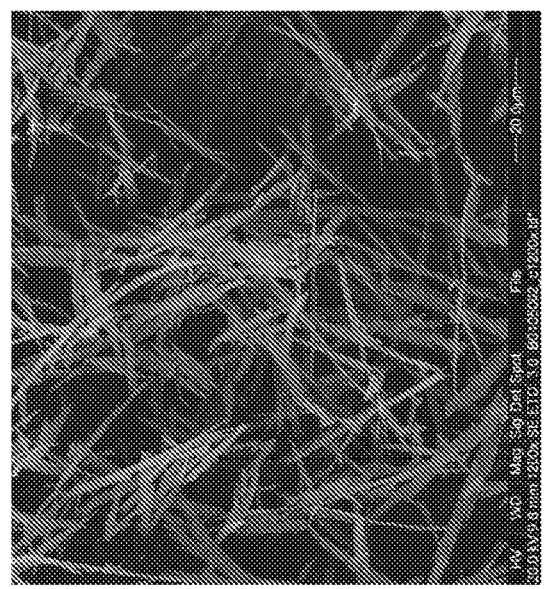
FIG. 5a is an SEM of tolterodine L-tartrate particles precipitated in Example C1.
Figure 5D:
FIG. 5d is an SEM of tolterodine L-tartrate particles precipitated in Example C4.
Figure 5E:
FIG. 5e is an SEM of tolterodine L-tartrate particles precipitated in Example C5.
Figure 5C:
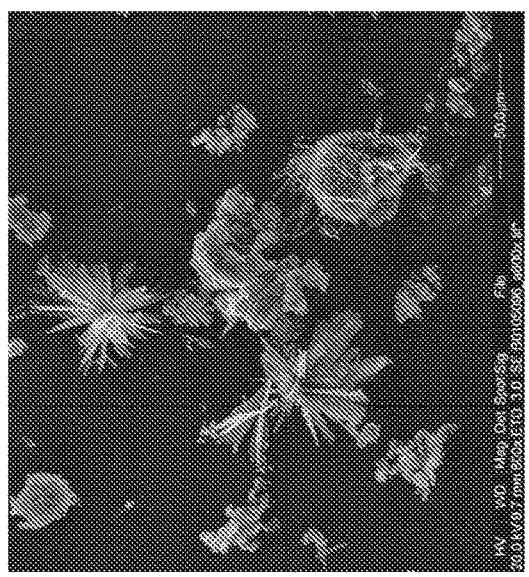
FIG. 5c is an SEM of tolterodine L-tartrate particles precipitated in Example C3.
Figure 6:
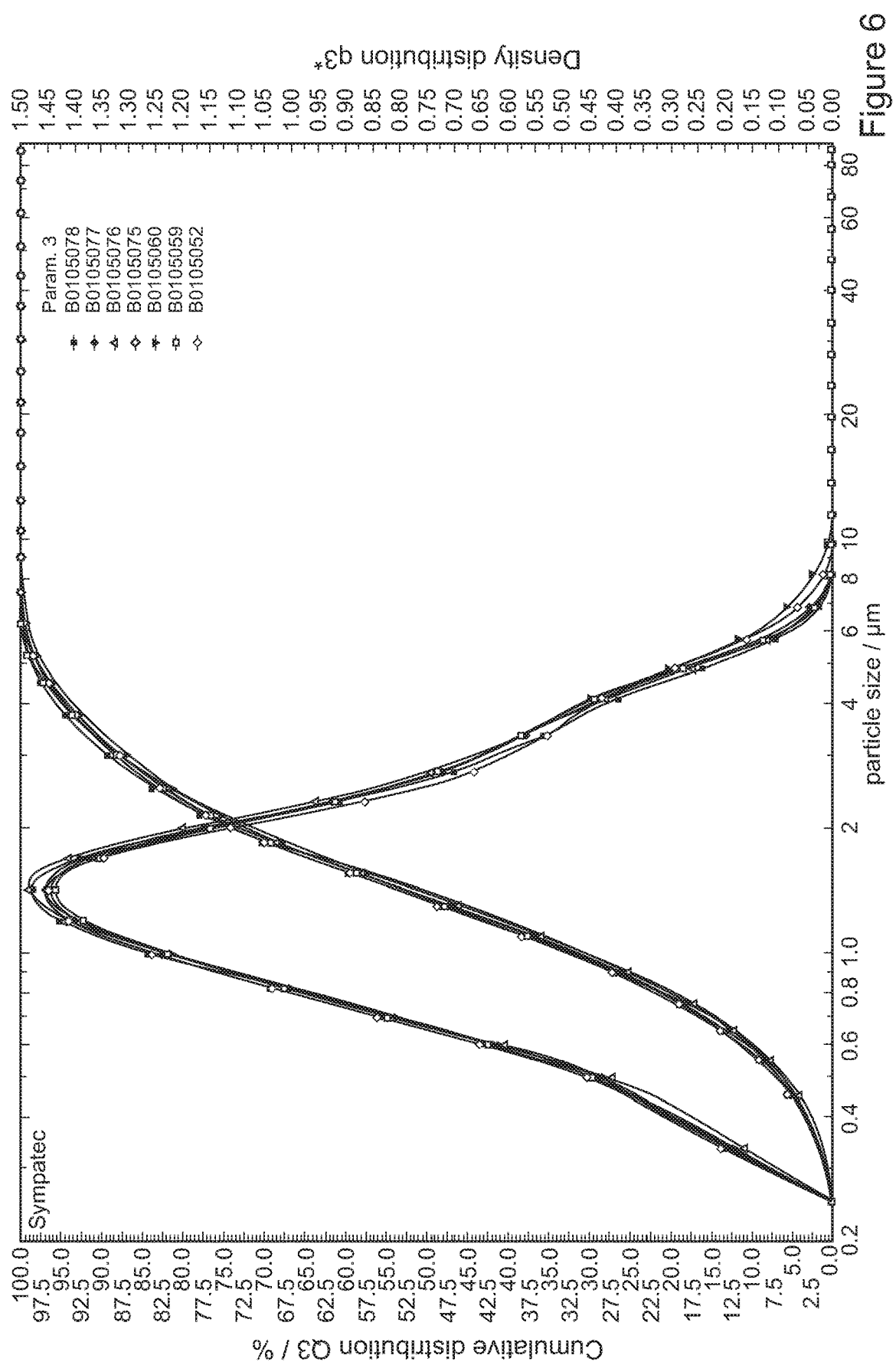
FIG. 6 shows particle size distributions of tolterodine L-tartrate particles precipitated in Example 31.

With reference to FIG. 3b, the particle size analysis of milled tolterodine L-tartrate shows a relatively broad distribution, with a relatively high percentage of particles larger than 5 microns (approx 20%).

Examples 1 to 33—Tolterodine
L-Tartrate/Examples C1 to C5

Experiments were conducted with the object of forming advantageously inhalable or insufflable particles of Tolterodine L-tartrate using supercritical anti-solvent (SAS) precipitation.

Tolterodine L-tartrate forms acicular (needle-like) crystals. Acicular particles grow extremely fast in one dimension. This presents particular challenges in the context of precipitation of inhalable or insufflable particles. Specific particle formation conditions for providing readily inhalable or insufflable particles, in particular particles with $D_{50}$ and $D_{90}$ percentiles between 1 to 4 μm and 2 to 10 μm and volume mean diameter <7 μm, more preferably <5 μm respectively were investigated.

The method used to generate particles of inhalable tolterodine L-tartrate was a SAS (Supercritical Anti-Solvent) process For each example, tolterodine L-tartrate was dissolved in methanol.

A stream of the solution of tolterodine L-tartrate was contacted with a stream of supercritical or near critical carbon dioxide in a precipitation chamber, with the help of a mixing nozzle arrangement, to form particles of tolterodine L-tartrate. The effect of a range of particle formation conditions on particle precipitation was examined in Examples 1 to 33, in which particle formation conditions were varied.

Particle formation conditions that were varied are listed in Table 1, together with particle size results. In more detail, Table 1 refers to the following particle formation conditions/results:

- The volume of the precipitation chamber (“Chamber volume”), indicated in millilitres (ml).
- The type of mixing nozzle arrangement (“Nozzle Type”)—in a first nozzle arrangement (Type I) carbon dioxide was arranged to impinge on a stream of the solution to provide high shear, whereas in a second nozzle arrangement the carbon dioxide and the solution were co-fed into the precipitation chamber via a nozzle having co-axial passages which terminate adjacent to one another, providing less shear, there being a first variant with a carbon dioxide orifice diameter of 750 micrometres (Type II) and a second variant with a carbon dioxide orifice diameter of 200 micrometres (Type III).

The concentration of tolterodine L-tartrate in the methanol solution ("Drug Solution Concentration"), indicated in milligrams per millilitre of methanol (mg/ml).

The temperature of the stream of carbon dioxide ("$CO_2$ T") indicated in degrees Celsius (° C.)

The atmospheric pressure of the stream of carbon dioxide ("$CO_2$ p") indicated in bars (bar)

The density of the stream of carbon dioxide ("$CO_2$ Density") indicated in grams per cubic centimetre (g/cm$^3$)

The flow rate of the solution of tolterodine L-tartrate into the precipitation chamber ("Drug Solution Flow") indicated in grams per minute (g/min)

The flow rate of carbon dioxide into the precipitation chamber ("$CO_2$ Flow") indicated in grams per minute (g/min)

The velocity of the carbon dioxide stream entering the precipitation chamber ("$CO_2$ Velocity") indicated in metres per second (m/s)

The ratio ("Mass Fraction Ratio Flows") of the mass fraction of the carbon dioxide flow into the precipitation chamber ($CO_2$ Flow/[$CO_2$ Flow+Drug Solution Flow]) over the mass fraction of the solution of tolterodine L-tartrate solution flow into the precipitation chamber (Drug Solution Flow/[$CO_2$ Flow+Drug Solution Flow]), dimensionless.

The particle diameter where a cumulative particle diameter distribution of the precipitated tolterodine L-tartrate particles reaches 50% by volume, i.e. 50% by volume of the particles have a smaller diameter than this value, and 50% by volume of the particles have a larger diameter than this value ("$D_{50}$"), indicated in micrometres (μm).

The particle diameter where a cumulative particle diameter distribution of the precipitated tolterodine L-tartrate particles reaches 90% by volume, i.e. 90% by volume of the particles have a smaller diameter than this value, and 10% by volume of the particles have a larger diameter than this value ("$D_{90}$"), indicated in micrometres (μm).

The volume mean diameter ("VMD") of the precipitated tolterodine L-tartrate particles, indicated in micrometres (μm).

TABLE 1

| Example No | Vessel Volume (ml) | Nozzle Type | Drug Solution Concentration (mg/ml) | $CO_2$ T (° C.) | $CO_2$ p (bar) | $CO_2$ Density (g/cm$^3$) | Drug Solution Flow (g/min) | $CO_2$ Flow (g/min) | $CO_2$ Velocity (m/s) | Mass Ratio Flows | $D_{50}$ (μm) | $D_{90}$ (μm) | VMD (μm) |
|---|---|---|---|---|---|---|---|---|---|---|---|---|---|
| 1 | 600 | Type I | 31.25 | 40 | 85 | 0.353 | 0.16 | 36 | 54.13 | 226 | 1.2 | 2.5 | 1.4 |
| 2 | 600 | Type I | 41.67 | 40 | 85 | 0.353 | 0.16 | 36 | 54.13 | 226 | 1.2 | 2.7 | 1.5 |
| 4 | 600 | Type I | 31.25 | 35 | 85 | 0.419 | 0.16 | 36 | 45.60 | 226 | 2.1 | 5.7 | 2.7 |
| 5 | 50 | Type II | 31.25 | 40 | 85 | 0.353 | 0.32 | 20 | 30.07 | 63 | 2.2 | 5.1 | 2.7 |
| 6 | 50 | Type II | 31.25 | 40 | 85 | 0.353 | 0.16 | 20 | 30.07 | 126 | 2.2 | 5.0 | 2.6 |
| 7 | 50 | Type III | 31.25 | 40 | 85 | 0.353 | 0.32 | 20 | 30.07 | 63 | 2.2 | 5.8 | 2.9 |
| 8 | 200 | Type I | 31.25 | 40 | 85 | 0.353 | 0.32 | 36 | 54.13 | 177 | 1.2 | 3.2 | 1.6 |
| 9 | 200 | Type I | 31.25 | 40 | 85 | 0.353 | 0.32 | 20 | 30.07 | 63 | 2.2 | 5.4 | 2.7 |
| 10 | 200 | Type I | 31.25 | 40 | 85 | 0.353 | 0.08 | 20 | 30.07 | 249 | 2.4 | 8.4 | 3.7 |
| 11 | 200 | Type I | 31.25 | 40 | 85 | 0.353 | 0.16 | 20 | 30.07 | 126 | 1.5 | 5.2 | 4.8 |
| 12 | 200 | Type I | 31.25 | 40 | 85 | 0.353 | 0.48 | 20 | 30.07 | 42 | 2.0 | 8.4 | 3.5 |
| 13 | 200 | Type I | 31.25 | 40 | 85 | 0.353 | 0.63 | 20 | 30.07 | 32 | 3.4 | 9.3 | 4.4 |
| 14 | 200 | Type I | 5 | 40 | 85 | 0.353 | 0.16 | 20 | 30.07 | 126 | 1.8 | 6.3 | 6.6 |
| 15 | 200 | Type I | 10 | 40 | 85 | 0.353 | 0.16 | 20 | 30.07 | 126 | 1.4 | 4.1 | 2.0 |
| 16 | 200 | Type I | 31.25 | 35 | 85 | 0.612 | 0.16 | 20 | 17.35 | 126 | 2.2 | 8.2 | 3.6 |
| 17 | 200 | Type I | 31.25 | 40 | 120 | 0.718 | 0.16 | 36 | 26.61 | 226 | 2.7 | 8.1 | 3.7 |
| 18 | 200 | Type I | 31.25 | 35 | 80 | 0.419 | 0.16 | 36 | 45.60 | 226 | 2.1 | 5.7 | 2.7 |
| 19 | 200 | Type I | 31.25 | 45 | 85 | 0.281 | 0.16 | 36 | 68.00 | 226 | 1.2 | 2.7 | 1.5 |
| 20 | 200 | Type I | 31.25 | 50 | 95 | 0.330 | 0.16 | 36 | 57.90 | 226 | 1.2 | 2.8 | 1.5 |
| 21 | 200 | Type I | 31.25 | 40 | 85 | 0.353 | 0.79 | 36 | 54.13 | 46 | 2.7 | 6.9 | 3.3 |
| 22 | 200 | Type I | 31.25 | 40 | 75 | 0.232 | 0.16 | 36 | 82.36 | 226 | 1.1 | 2.4 | 1.4 |
| 23 | 200 | Type I | 31.25 | 60 | 105 | 0.322 | 0.16 | 36 | 59.34 | 226 | 1.3 | 2.7 | 1.5 |
| 24 | 200 | Type I | 31.25 | 70 | 110 | 0.294 | 0.16 | 36 | 64.99 | 226 | 1.4 | 2.7 | 1.6 |
| 25 | 200 | Type I | 31.25 | 80 | 125 | 0.318 | 0.16 | 36 | 60.09 | 226 | 1.7 | 3.6 | 2.0 |
| 26 | 200 | Type I | 31.25 | 50 | 150 | 0.700 | 0.16 | 36 | 27.30 | 226 | 2.9 | 8.2 | 3.8 |
| 27 | 200 | Type I | 31.25 | 80 | 200 | 0.594 | 0.16 | 36 | 32.17 | 226 | 3.1 | 8.9 | 4.2 |
| 28 | 50 | Type I | 31.25 | 40 | 85 | 0.353 | 0.16 | 20 | 30.07 | 126 | 2.9 | 9.3 | 4.7 |
| 29 | 2000 | Type I | 31.25 | 40 | 85 | 0.353 | 0.88 | 200 | 300.73 | 226 | 1.8 | 4.6 | 2.3 |
| 30 | 2000 | Type I | 31.25 | 40 | 85 | 0.353 | 1.60 | 200 | 300.73 | 126 | 1.6 | 4.4 | 4.5 |
| 31 | 2000 | Type I | 31.25 | 50 | 95 | 0.330 | 0.88 | 200 | 321.69 | 226 | 1.3 | 3.3 | 3.5 |
| 32 | 2000 | Type I | 31.25 | 60 | 105 | 0.322 | 0.88 | 200 | 329.68 | 226 | 1.4 | 3.3 | 3.5 |
| 33 | 2000 | Type I | 31.25 | 50 | 110 | 0.503 | 0.88 | 200 | 211.05 | 226 | 2.0 | 5.0 | 2.6 |
| C1 | 200 | Type I | 31.25 | 40 | 200 | 0.840 | 0.32 | 36 | 22.75 | 113 | >10 | | |
| C2 | 200 | Type I | 31.25 | 40 | 75 | 0.232 | 0.16 | 20 | 45.76 | 126 | >10 | | |
| C3 | 200 | Type I | 31.25 | 40 | 200 | 0.840 | 0.16 | 20 | 37.78 | 126 | 3.9 | 17.9 | 6.0 |
| C4 | 200 | Type I | 31.25 | 40 | 150 | 0.780 | 0.16 | 36 | 24.50 | 226 | 3.8 | 11.9 | 5.4 |
| C5 | 200 | Type 1 | 31.25 | 50 | 200 | 0.784 | 0.16 | 36 | 24.37 | 226 | 4.3 | 13.0 | 5.9 |

After extensive experimental studies with SAS processing involving alternative temperatures and pressures and consideration of a range of different solvent and co-solvent systems, we have established a set of particle formation conditions that enables tolterodine particles with the required characteristics to be prepared (see Examples).

Examples 1 to 33 each produced, fine, free flowing powders. These Examples show that readily inhalable or insufflable particles of tolterodine L-tartrate, in particular particles with $D_{50}$ and $D_{90}$ percentiles between 1 to 4 μm and 2 to 10 μm and volume mean diameter <7 μm, more preferably <5 μm, were obtained when:

the ratio of the mass fraction of contacted carbon dioxide to the mass fraction of contacted tolterodine solution was 30 or more and the carbon dioxide had a density in the range of from 0.30 to 0.75 g/cm$^3$; and/or
- the ratio of the mass fraction of contacted carbon dioxide to the mass fraction of contacted tolterodine solution was 200 or more.

Surprisingly, it was found that at higher carbon dioxide flow (ratio of mass fraction 200 or more), it was possible to produce inhalable particles at higher temperature (50° C., 60° C., 70° C. and 80° C.), higher pressure (125 bar, 150 bar and 200 bar) and solution flow rate (0.79 g/min). At lower carbon dioxide flow, a density of from 0.30 to 0.75 g/cm$^3$ of the carbon dioxide, which corresponds with narrower temperature and pressure ranges, assisted advantageous particle formation.

Confirmation of chemical and polymorphic identity of the particles obtained in Example 1 was assessed by both powder X-ray diffraction (PXRD) and differential scanning calorimetry (DSC). Specifically, assessment of crystallinity was carried out using the Bruker AXS (Karisruhe, Germany) model D8 Advance X-Ray Diffractometer. Data was collected between 2° and 40° 2θ in a stepwise mode (step: 0.04°/min). DSC experiments were run on a TA Instruments Q2000 DSC equipped with RCS90 refrigerated cooling system at 10° C./min and TGA experiments were carried out on TA Instruments Q5000 TGA at 10° C./min.

FIGS. 1, 2*a* and 2*b* show the Powder X-ray Diffraction pattern and thermal analysis of particles produced in Example 1.

The PXRD analysis shows that the SCF processed material is crystalline with characteristic peaks of tolterodine L-tartrate.

The DSC (Differential Scanning Calorimetry) data show that the particles displayed a sharp melting endotherm of 214° C. (onset) that decomposed on melt.

Accordingly, it can be concluded that the particles consist of the crystalline form of tolterodine L-tartrate.

SEM (scanning electron microscope) examination of the particles of Example 1 showed a torpedo shaped morphology for particles (FIG. 3*a*) with a narrow particle size distribution suitable for respiratory drug delivery. Notably, these particles have a different shape to the milled particles of FIGS. 10*c* and 10*d* and do not suffer from the agglomeration seen in the milled particles.

The particle size distribution for the material is more regular, with a narrower particle size spread when compared with milled material. All particles appear independent without any 'smaller' particle adherence to the surfaces of other particles, a reflection of the improved and smoother surface topography, which facilitates particle aerosolisation.

A comparison between FIGS. 3*b* and 3*c* illustrates the markedly narrower particle size distributions obtained at three aerosolisation pressures for the SCF processed material.

Chemical purity of the particles obtained in Example 1 was assessed by High Pressure Liquid Chromatography using a Waters 2790 separations module coupled with a Waters 996 photodiode array detector. The HPLC method used a $C_{18}$ column (5 μm, 150×4.6 mm) protected with a pre-column. The mobile phase consisted of acetonitrile-20 mM ammonium acetate (50:50 v/v), using a flow rate of 1.2 ml/min. The sample eluted at 3.7 min.

With reference to FIGS. 4*a* and 4*b*, data shows that the processing of Example 1 did not significantly degrade tolterodine L-tartrate when analysed against a calibration line ($y=9933x+1025.1$, $R^2=0.9985$). Actual peak area=533719, predicted peak area from calibration line (produced from tolterodine L-tartrate starting material) =499662.

Referring again to Table 1, Examples C1 to C5 show that, outside the above-identified operating parameters, the tolterodine L-tartrate particles had a $D_{90}$ in excess of 10 μm and in some cases a $D_{50}$ in excess of 4 μm. Such particles would be less suitable for inhalation or insufflation on account of their larger size, or indeed may be wholly unsuitable.

With reference to FIG. 5*a*, the SEM of the particles obtained from example C1 shows a majority of the particles is clearly larger than 10 μm. No full particle size analysis is provided for this sample as particle size analysis of these particles would result in communition of particles during analysis and therefore no meaningful data would be collected.

With reference to FIG. 5*b*, the SEM of the particles obtained from example C2 also shows a majority of the particles is clearly larger than 10 μm. This precipitate was a free flowing powder, but no full particle size analysis is provided for this sample as particle size analysis of these particles resulted in communition of particles during analysis and therefore no meaningful data could be collected.

With reference to FIG. 5*c*, the SEM of the particles obtained from example C3 were a fine, free flowing powder. A particle size analysis was conducted and confirmed a $D_{90}$ in excess of 10 μm.

With reference to FIG. 5*d*, the SEM of the particles obtained from example C4 were a fine, free flowing powder. A particle size analysis was conducted and confirmed a $D_{90}$ in excess of 10 μm.

With reference to FIG. 5*e*, the SEM of the particles obtained from example C5 were a fine, free flowing powder. A particle size analysis was conducted and confirmed a $D_{90}$ in excess of 10 μm and a $D_{50}$ in excess of 4 μm.

Example 34—Hydroxymethyl Tolterodine

A further experiment was conducted to prepare inhalable particles of hydroxymethyl tolterodine.

Hydroxymethyl tolterodine was precipitated, in the general manner of Examples 1 to 33, from acetonitrile solution (50.0 mg/ml) using a carbon dioxide temperature of 40° C., a carbon dioxide pressure of 85 bar, a carbon dioxide density of 0.353, a hydroxymethyl tolterodine solution flow of 0.32 g/min and carbon dioxide flow of 36 g/min. The product was a fine, free flowing powder that had $D_{50}$ and $D_{90}$ percentiles of 1.2 μm and 3.1 μm and volume mean diameter 1.5 μm respectively. The sample was amorphous by PXRD.

Example 35—Batch Consistency

The results of reproducibility of seven batches of tolterodine L-tartrate produced using the same conditions as in Example 1 are shown in FIG. 6 in the form of a particle size distribution curve. Particle size analysis of the product was carried out using a Sympatec Helos Particle Size Analyser using an aerosolisation pressure of 4 bar.

Particles possessed a median diameter of $D_{50}=1.4$ µm with a percentiles diameter of $D_{90}=3.3$ µm and a volume mean diameter (VMD)=1.7 µm. These data demonstrate the excellent reproducibility under the conditions of Example 1 process and confirm the suitability of the particle size distribution for respiratory drug delivery applications.

Example 36—Bioavailability of Inhaled Studies in Rats for Tolterodine L-Tartrate Precipitated in Example 1

Three dose groups of Sprague-Dawkley male rats (each dose group contained 5 rats), weight range 300-350 g were obtained from Charles River (UK). All procedures were conducted by Huntington Life Sciences in compliance with the United Kingdom Animals (Scientific Procedures) Act 1986. The study complied with all applicable sections of the Act and the associated Codes of Practices for the Housing and Care used in Scientific procedures and the Humane Killing of Animals under Schedule 1 to the Act, issued under Section 21 of the Act.

Tolterodine L-tartrate, produced as described in Example 1 for aerosol administration, was prepared in a capsule actuator which is able to load, pierce, aerosolise the contents and discharge individual capsules through a sequential mechanised cycle (manufactured by Huntington Life Sciences, Cambs, UK). Compressed air is used to aerosolise the contents of the caps. The rats were placed in a carousel-style, nose only, exposure chamber and allowed to inhale for 10 minutes.

Three different dose levels of aerosolised tolterodine L-tartrate of 0.1 mg/kg, 0.3 mg/kg and 1 mg/kg were studied. Blood samples were taken pre-dose and 0.17, 0.33, 0.5, 1, 2, 4, 8, 12 and 24 hours post aerosol drug treatment.

Figure 7:
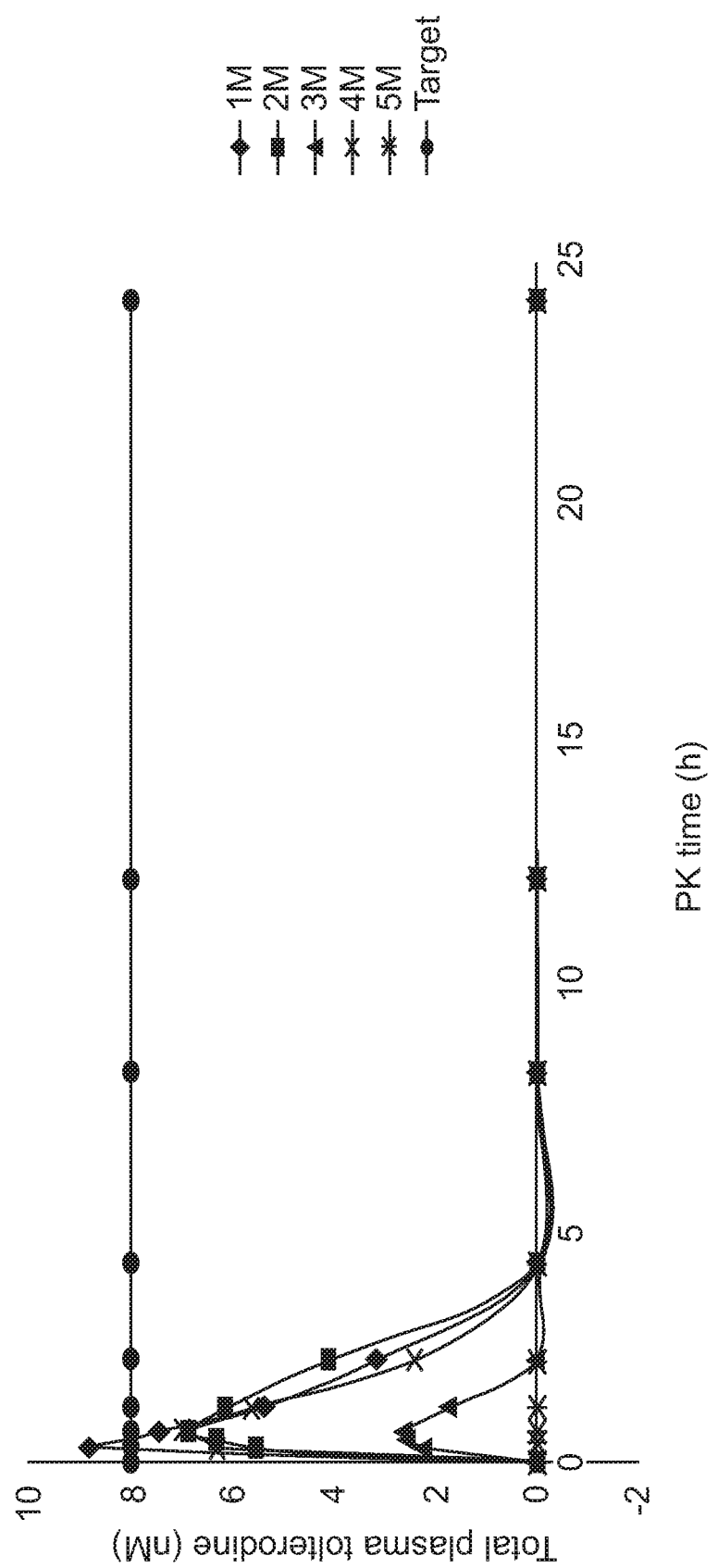
FIG. 7 shows pharmacokinetic data for Group 1 (0.1 mg/kg dose for 10 minutes) in Example 32

Aerosol administration (FIGS. 7, 8 and 9) produced an instant rise in tolterodine plasma concentration. The data show that exposure was rapid with about 80% peak exposure at the first measurable data point. The exposure target of 8 nM was detected in four out of the five rats in group 2 at 0.3 mg/kg dose level with rapid elimination of the drug from the plasma in less than 10 minutes in all rats in the 3 groups.

Example 37—In Vitro Aerosolisation Studies of DPI Formulation of Tolterodine L-Tartrate/Powdered Lactose Blend (1:9w/w)

Anderson Cascade Impactor (ACI) studies of the aerosolisation behaviour of two batches of pharmaceutical powder compositions were conducted. In particular the studies determined the total emitted dose (TED), fine particle dose (FPD), fine particle fraction as a percentage of TED (FPF %), mass median aerodynamic diameter (MMAD) and geometric standard deviation (GSD) of two batches of tolterodine/lactose pharmaceutical powder compositions. A comparison with milled compositions was also conducted.

Pharmaceutical powder compositions were prepared by blending 2 g tolterodine L-tartrate obtained by the method of Example 1 with 18 g α-lactose monohydrate (size fraction 63-90 µm) in a Turbula Mixer for 30 minutes. After blending 10 mg of powder blend was filled into size 3 hard gelatin capsules and individual capsules were fitted into a Cyclohaler dry powder inhaler device prior to activating the device with the ACI connected and in operation.

Three capsules each containing a 10:90% w/w drug content:lactose blend were required for each 'run' at a single flow rate of 90 L/min.

The dose emission data are shown in Table 2 and Table 3 for batch 1 and 2 respectively. The lactose powder used was Inhalable Lactose (Respitose, supplied by DFE Pharma Limited).

TABLE 2

|  | 90 L/min |
| --- | --- |
| Loaded dose (µg) | 1000.00 |
| TED (µg) | 660.00 |
| FPD (µg) | 460.00 |
| FPF % of TED | 68.91 |
| MMAD(um) | 1.20 |
| GSD | 2.30 |

With reference to Table 2, there is shown the mean (SD) data obtained from ACI at 90 L/min for batch 1 normalised for 1 dose (nominal dose 1 mg). TED-Total Emitted Dose; FPD-Fine Particle Dose; FPF-Fine Particle Fraction, MMAD-Mass Median Aerodynamic Diameter and GSD-Geometric Standard Deviation.

TABLE 3

|  | 90 L/min |
| --- | --- |
| Loaded dose (µg) | 1000.00 |
| TED (µg) | 650.00 |
| FPD (µg) | 440.00 |
| FPF % of TED | 67.51 |
| MMAD (um) | 1.20 |
| GSD | 2.30 |

With reference to Table 3, there is shown the mean (SD) data obtained from ACI at 90 L/min for batch 2 normalised for 1 dose (nominal dose 1 mg). TED-Total Emitted Dose; FPD-Fine Particle Dose; FPF-Fine Particle Fraction, MMAD-Mass Median Aerodynamic Diameter and GSD-Geometric Standard Deviation.

The data in Tables 1 and 2 show generally good agreement between the aerosolisation of the two batches of the tolterodine dry powder formulation. The FPF % values at 90 L/min of 68.91 and 67.51% indicate very good performance of the tolterodine powder formulation.

The particles of Example 1 were thus found to perform especially well in a 'prototype' formulation and 'off the shelf inhaler device', with two batches showing a FPF of 68.91 and 67.51% of emitted dose.

A comparative figure for a micronised/milled 'prototype' formulation would be expected to be more around FPF % of 20-25%. With reference to FIG. 3b, particle size data also show that a much higher percentage of particles larger than 5 microns (approx 20% compared with 10%) are present in the micronised sample compared with the material of Example 1. The fact that one 5 micron sized particle has the same volume, and therefore mass, as ×1000 1 micron sized particles means that a much higher proportion of a dose of the micronised material is likely to be poorly deposited in the central and deep lung compartments of the respiratory tract compared with the material of Example 1.

Indeed this is confirmed by the following comparative data obtained from an identical cascade impactor study performed using, instead of the material of Example 1, milled tolterodine L-tartrate obtained according to the Comparative Example above and having a particle size distribution as shown in FIG. 3b.

TABLE 4

|  | 90 L/min |
| --- | --- |
| Loaded dose (µg) | 1000.00 |
| TED (µg) | 865.00 |
| FPD (µg) | 225.00 |
| FPF % of TED | 26.12 |
| MMAD (um) | 1.65 |
| GSD | 3.85 |

It can be concluded from Example 37 that the material of Examples 1 to 33, in particular of Example 1, is especially suitable for inhalation and insufflation. The material according to the Examples was shown to have a greatly superior FPF %.

Given the high FPF reported in Example 37, it is expected that the material, once inhaled or insufflated, provides for rapid absorption of tolterodine, at a faster rate than a comparable dose of micronized tolterodine. Smaller particles tend to be more readily absorbed. This is also consistent with the data obtained in Example 36.

Example 38—Pharmaceutical Use

Given the results of Examples 1 to 37, and the clinical efficacy of tolterodine demonstrated in the prior art, there are provided pharmaceutical compositions comprising the material of any of Examples 1 to 33, e.g. a pharmaceutical composition as described in Example 37, for use in treating, in a human or other mammal, a disorder selected from the group consisting of: urinary disorder, asthma, COPD, and allergic rhinitis by inhalation or insufflation, in particular pulmonary delivery.

There will be provided a pharmaceutical composition according to the invention, e.g. as described in Example 37, for treatment, in a human or other mammal, of urinary disorder by inhalation or insufflation. The composition will be therapeutically effective with a minimum of deleterious side effects.

There will be provided a pharmaceutical composition according to the invention, e.g. as described in Example 37, for treatment, in a human or other mammal, of asthma by inhalation or insufflation. The composition will be therapeutically effective with a minimum of deleterious side effects.

There will be provided a pharmaceutical composition according to the invention, e.g. as described in Example 37, for treatment, in a human or other mammal, of COPD by inhalation or insufflation. The composition will be therapeutically effective with a minimum of deleterious side effects.

There will be provided a pharmaceutical composition according to the invention, e.g. as described in Example 37, for treatment, in a human or other mammal, of allergic rhinitis by inhalation or insufflation. The composition will be therapeutically effective with a minimum of deleterious side effects.

Suitably, the compositions will provide rapid symptomatic relief or fast onset of tolterodine as hereinabove defined. For example, there will be provided a pharmaceutical composition according to the invention, e.g. as described in Example 37, for treatment providing rapid relief from urinary incontinence, in particular urge incontinence, stress incontinence or mixed incontinence, in a human or other mammal, by inhalation or insufflation. The composition will be effective with a minimum of deleterious side effects.

The invention claimed is:

1. A method of forming tolterodine L-tartrate particles by supercritical anti-solvent precipitation, the method comprising:
   contacting an anti-solvent stream with a tolterodine L-tartrate solution stream to form particles of tolterodine L-tartrate by supercritical anti-solvent precipitation,
   wherein the anti-solvent stream is arranged to impinge on the tolterodine L-tartrate solution stream,
   wherein the anti-solvent stream comprises supercritical $CO_2$,
   wherein the tolterodine L-tartrate solution stream comprises tolterodine L-tartrate dissolved in a solvent,
   wherein,
      when the supercritical $CO_2$ has a $CO_2$ density of 0.30 to 0.75 g/cm$^3$, the anti-solvent stream and the tolterodine L-tartrate solution stream are contacted such that the ratio of the mass fraction of contacted supercritical $CO_2$ to the mass fraction of contacted tolterodine L-tartrate solution is 30 or more, and
      when the supercritical $CO_2$ has a $CO_2$ density of 0.20 to less than 0.30 g/cm$^3$, the anti-solvent stream and the tolterodine L-tartrate solution stream are contacted such that the ratio of the mass fraction of contacted supercritical $CO_2$ to the mass fraction of contacted tolterodine L-tartrate solution is 200 or more, and
   wherein the particles of tolterodine L-tartrate have a $D_{50}$ of 1 µm to 4 µm and a $D_{90}$ of 2 µm to 10 µm.

2. The method of claim 1, wherein the solvent comprises methanol.

3. The method of claim 1, wherein the anti-solvent stream and the tolterodine L-tartrate solution stream are contacted such that dispersion and extraction of a solvent system of the tolterodine L-tartrate solution occur substantially simultaneously by the action of the anti-solvent.

4. The method of claim 1, wherein the anti-solvent stream has a velocity that is higher than a velocity of the tolterodine L-tartrate solution stream.

5. The method of claim 1, wherein a velocity ratio between the anti-solvent stream and the tolterodine L-tartrate solution stream is in the range of from 500:1 to 1000:1.

6. The method of claim 1, wherein the anti-solvent stream and the tolterodine L-tartrate solution stream are introduced into a precipitation chamber via respective passages with respective outlets, the outlets being arranged relative to one another such that anti-solvent stream introduced through a first passage and the tolterodine L-tartrate solution stream introduced through a second passage both enter the precipitation chamber at substantially the same point, which is substantially the point at which the anti-solvent stream and the tolterodine L-tartrate solution stream contact.

7. The method of claim 1, wherein the anti-solvent stream and the tolterodine L-tartrate solution stream are co-fed into a precipitation chamber via a nozzle having co-axial passages that terminate adjacent to one another.

* * * * *